US008965087B2

(12) United States Patent  
Arnaud et al.

(10) Patent No.: US 8,965,087 B2  
(45) Date of Patent: *Feb. 24, 2015

(54) SYSTEM AND METHOD OF PREDICTING FUTURE FRACTURES

(71) Applicant: ImaTx, Inc., Bedford, MA (US)

(72) Inventors: Claude D. Arnaud, Mill Valley, CA (US); Philipp Lang, Lexington, MA (US); Siau-Way Liew, Pinole, CA (US); Daniel Steines, Lexington, MA (US); Rene Vargas-Voracek, Sunnyvale, CA (US)

(73) Assignee: ImaTx, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/094,040

(22) Filed: Dec. 2, 2013

(65) Prior Publication Data  
US 2014/0093149 A1 Apr. 3, 2014

Related U.S. Application Data

(63) Continuation of application No. 11/228,126, filed on Sep. 16, 2005, now Pat. No. 8,600,124.

(60) Provisional application No. 60/610,447, filed on Sep. 16, 2004.

(51) Int. Cl.  
*G06K 9/00* (2006.01)  
*A61B 5/00* (2006.01)  
(Continued)

(52) U.S. Cl.  
CPC .............. *A61B 5/7275* (2013.01); *A61B 6/505* (2013.01); *G06T 7/0012* (2013.01); *G06T 7/401* (2013.01); *G06T 7/602* (2013.01); *G06T 7/606* (2013.01);

(Continued)

(58) Field of Classification Search  
None  
See application file for complete search history.

(56) References Cited

U.S. PATENT DOCUMENTS 2,274,808 A 3/1942 Rinn ................................ 250/69  
3,924,133 A 12/1975 Reiss ............................. 250/408  
(Continued)

FOREIGN PATENT DOCUMENTS

CA 2342344 3/2000 ............... G06K 9/00  
DE 19853965 5/2000 ................ A61F 2/28  
(Continued)

OTHER PUBLICATIONS

Barker, "Case Method: Entity Relationship Modeling" (Computer Aided Systems Engineering), 1$^{st}$ Ed., Addison-Wesley Longman Pub. Co., Inc., publisher, 2 pages (Abstract Pages Only) (1990).

(Continued)

*Primary Examiner* — Nancy Bitar  
(74) *Attorney, Agent, or Firm* — Sunstein Kann Murphy & Timbers LLP

(57) ABSTRACT

Methods of predicting fracture risk of a patient include: obtaining an image of a bone of the patient; determining one or more bone structure parameters; predicting a fracture line with the bone structure parameter; predicting a fracture load at which a fracture will happen; estimating body habitus of the patient; calculating a peak impact force on the bone when the patient falls; and predicting a fracture risk by calculating the ratio between the peak impact force and the fracture load. Inventive methods also include determining the effect of a candidate agent on any subject's risk of fracture.

23 Claims, 13 Drawing Sheets

(51) Int. Cl.
*A61B 6/00* (2006.01)
*G06T 7/00* (2006.01)
*G06T 7/40* (2006.01)
*G06T 7/60* (2006.01)
*A61B 8/08* (2006.01)
*G01R 33/54* (2006.01)

(52) U.S. Cl.
CPC ............... *A61B 5/4509* (2013.01); *A61B 6/52* (2013.01); *A61B 8/52* (2013.01); *G01R 33/54* (2013.01); *G06T 2207/10116* (2013.01); *G06T 2207/20104* (2013.01); *G06T 2207/30008* (2013.01); *A61B 2576/02* (2013.01)
USPC ........................................................ 382/128

(56) References Cited

U.S. PATENT DOCUMENTS

| | | | | |
|---|---|---|---|---|
| 4,012,638 A | 3/1977 | Altschuler et al. | ............ | 250/491 |
| 4,126,789 A | 11/1978 | Vogl et al. | ..................... | 250/505 |
| 4,233,507 A | 11/1980 | Volz | .............................. | 250/252 |
| 4,251,732 A | 2/1981 | Fried | ........................... | 250/479 |
| 4,298,800 A | 11/1981 | Goldman | ................... | 250/445 T |
| 4,356,400 A | 10/1982 | Polizzi et al. | ................. | 378/138 |
| 4,400,827 A | 8/1983 | Spears | .......................... | 378/207 |
| 4,593,400 A | 6/1986 | Mouyen | ........................... | 378/99 |
| 4,649,561 A | 3/1987 | Arnold | .......................... | 378/207 |
| 4,686,695 A | 8/1987 | Macovski | ..................... | 378/146 |
| 4,721,112 A | 1/1988 | Hirano et al. | .................. | 128/659 |
| 4,782,502 A | 11/1988 | Schultz | ............................ | 378/18 |
| 4,922,915 A | 5/1990 | Arnold et al. | ............ | 128/653 R |
| 4,956,859 A | 9/1990 | Lanza et al. | ................... | 378/157 |
| 4,985,906 A | 1/1991 | Arnold | ............................ | 378/18 |
| 5,001,738 A | 3/1991 | Brooks | .......................... | 378/170 |
| 5,090,040 A | 2/1992 | Lanza et al. | ..................... | 378/62 |
| 5,122,664 A | 6/1992 | Ito et al. | ...................... | 250/327.2 |
| 5,127,032 A | 6/1992 | Lam et al. | ..................... | 378/189 |
| 5,150,394 A | 9/1992 | Karellas | ........................... | 378/62 |
| 5,172,695 A | 12/1992 | Cann et al. | ................. | 128/653.1 |
| 5,187,731 A | 2/1993 | Shimura | .......................... | 378/207 |
| 5,200,993 A | 4/1993 | Wheeler et al. | ................. | 379/96 |
| 5,222,021 A | 6/1993 | Feldman et al. | ........... | 364/413.14 |
| 5,228,445 A | 7/1993 | Pak et al. | ................. | 128/660.01 |
| 5,235,628 A | 8/1993 | Kalender | ......................... | 378/207 |
| 5,247,934 A | 9/1993 | Wehrli et al. | ............... | 128/653.2 |
| 5,270,651 A | 12/1993 | Wehrli | ............................ | 324/308 |
| 5,271,401 A | 12/1993 | Fishman | ......................... | 128/654 |
| 5,281,232 A | 1/1994 | Hamilton et al. | ................ | 606/130 |
| 5,320,102 A | 6/1994 | Paul et al. | ................. | 128/653.2 |
| 5,335,260 A | 8/1994 | Arnold | .......................... | 378/207 |
| 5,384,643 A | 1/1995 | Inga et al. | ....................... | 358/403 |
| 5,476,865 A | 12/1995 | Panetta et al. | .................. | 514/369 |
| 5,493,593 A | 2/1996 | Müller et al. | ..................... | 378/19 |
| 5,493,601 A | 2/1996 | Fivez et al. | .................... | 378/207 |
| 5,513,240 A | 4/1996 | Hausmann et al. | ........... | 378/170 |
| 5,521,955 A | 5/1996 | Gohno et al. | ...................... | 378/18 |
| 5,533,084 A | 7/1996 | Mazess | ............................ | 378/54 |
| 5,537,483 A | 7/1996 | Stapleton et al. | .............. | 382/309 |
| 5,562,448 A | 10/1996 | Mushabac | ..................... | 433/215 |
| 5,565,678 A | 10/1996 | Manian | ........................... | 250/252.1 |
| 5,592,943 A | 1/1997 | Buhler et al. | ............... | 128/661.03 |
| 5,594,775 A | 1/1997 | Hangartner | ..................... | 378/207 |
| 5,600,574 A | 2/1997 | Reitan | ............................ | 364/552 |
| 5,657,369 A | 8/1997 | Stein et al. | ...................... | 378/208 |
| 5,673,298 A | 9/1997 | Mazess | ............................ | 378/54 |
| 5,687,210 A | 11/1997 | Maitrejean et al. | ................ | 378/57 |
| 5,769,072 A | 6/1998 | Olsson et al. | ............... | 128/205.13 |
| 5,769,074 A | 6/1998 | Barnhill et al. | ................ | 128/630 |
| 5,772,592 A | 6/1998 | Cheng et al. | .................... | 600/407 |
| 5,852,647 A | 12/1998 | Schick et al. | ..................... | 378/53 |
| 5,864,146 A | 1/1999 | Karellas | ........................... | 250/581 |
| 5,886,353 A | 3/1999 | Spivey et al. | ............... | 250/370.09 |
| 5,915,036 A | 6/1999 | Grunkin et al. | .................. | 382/132 |
| 5,917,877 A | 6/1999 | Chiabrera et al. | .................. | 378/5.3 |
| 5,919,808 A | 7/1999 | Petrie et al. | ...................... | 514/372 |
| 5,931,780 A | 8/1999 | Giger et al. | ...................... | 600/407 |
| 5,945,412 A | 8/1999 | Fuh et al. | ......................... | 514/176 |
| 5,948,692 A | 9/1999 | Miyauti et al. | ................. | 436/501 |
| 6,013,031 A | 1/2000 | Mendlein et al. | ............. | 600/442 |
| 6,029,078 A | 2/2000 | Weinstein et al. | ............. | 600/407 |
| 6,064,716 A | 5/2000 | Siffert et al. | ...................... | 378/53 |
| 6,077,224 A | 6/2000 | Lang et al. | ...................... | 600/437 |
| 6,108,635 A | 8/2000 | Herren et al. | ...................... | 705/2 |
| 6,156,799 A | 12/2000 | Hartke et al. | ................... | 514/573 |
| 6,178,225 B1 | 1/2001 | Zur et al. | ....................... | 378/98.2 |
| 6,205,348 B1 | 3/2001 | Giger et al. | ...................... | 600/407 |
| 6,215,846 B1 | 4/2001 | Mazess et al. | ...................... | 378/62 |
| 6,226,393 B1 | 5/2001 | Grunkin et al. | .................. | 382/128 |
| 6,246,745 B1 | 6/2001 | Bi et al. | .......................... | 378/54 |
| 6,248,063 B1 | 6/2001 | Barnhill et al. | ................ | 600/300 |
| 6,249,692 B1 | 6/2001 | Cowin | ............................ | 600/407 |
| 6,252,928 B1 | 6/2001 | MacKenzie | ....................... | 378/54 |
| 6,285,901 B1 | 9/2001 | Taicher et al. | .................. | 600/410 |
| 6,289,115 B1 | 9/2001 | Takeo | ............................ | 382/130 |
| 6,302,582 B1 | 10/2001 | Nord et al. | ...................... | 378/207 |
| 6,306,087 B1 | 10/2001 | Barnhill et al. | ................ | 600/300 |
| 6,306,822 B1 | 10/2001 | Kumagai et al. | | |
| 6,315,553 B1 | 11/2001 | Sachdeva et al. | ............... | 433/24 |
| 6,320,931 B1 | 11/2001 | Arnold | ............................ | 378/56 |
| 6,377,653 B1 | 4/2002 | Lee et al. | ......................... | 378/54 |
| 6,405,068 B1 | 6/2002 | Pfander et al. | ................. | 600/407 |
| 6,411,729 B1 | 6/2002 | Grunkin | .......................... | 382/132 |
| 6,430,427 B1 | 8/2002 | Lee et al. | ......................... | 600/407 |
| 6,442,287 B1 | 8/2002 | Jiang et al. | ...................... | 382/128 |
| 6,449,502 B1 | 9/2002 | Ohkubo | ........................... | 600/407 |
| 6,463,344 B1 | 10/2002 | Pavloskaia et al. | ............. | 700/98 |
| 6,490,476 B1 | 12/2002 | Townsend et al. | ............. | 600/427 |
| 6,501,827 B1 | 12/2002 | Takasawa | ........................ | 378/116 |
| 6,556,698 B1 | 4/2003 | Diano et al. | ..................... | 382/132 |
| 6,633,772 B2 | 10/2003 | Ford et al. | ...................... | 600/345 |
| 6,690,761 B2 | 2/2004 | Lang et al. | ........................ | 378/56 |
| 6,694,047 B1 | 2/2004 | Farrokhnia et al. | ............ | 382/132 |
| 6,717,174 B2 | 4/2004 | Karellas | ........................... | 250/582 |
| 6,775,401 B2 | 8/2004 | Hwang et al. | .................. | 382/131 |
| 6,799,066 B2 | 9/2004 | Steines et al. | .................. | 600/407 |
| 6,807,249 B2 | 10/2004 | Dinten et al. | ..................... | 378/54 |
| 6,811,310 B2 | 11/2004 | Lang et al. | ..................... | 378/169 |
| 6,824,309 B2 | 11/2004 | Robert-Coutant et al. | ... | 378/207 |
| 6,829,378 B2 | 12/2004 | DiFilippo et al. | .............. | 382/128 |
| 6,835,377 B2 | 12/2004 | Goldberg et al. | ............. | 424/93.7 |
| 6,836,557 B2 | 12/2004 | Tamez-Pena et al. | ......... | 382/128 |
| 6,895,077 B2 | 5/2005 | Karellas et al. | ............... | 378/98.3 |
| 6,904,123 B2 | 6/2005 | Lang | ............................ | 378/54 |
| 6,934,590 B2 | 8/2005 | Ogawa | ............................ | 700/19 |
| 6,975,894 B2 | 12/2005 | Wehrli et al. | .................. | 600/407 |
| 7,050,534 B2 | 5/2006 | Lang | ............................ | 378/54 |
| 7,058,159 B2 | 6/2006 | Lang et al. | ....................... | 378/54 |
| 7,079,681 B2 | 7/2006 | Lee et al. | ........................ | 382/162 |
| 7,088,847 B2 | 8/2006 | Craig et al. | ...................... | 382/110 |
| 7,120,225 B2 | 10/2006 | Lang et al. | ....................... | 378/54 |
| 7,184,814 B2 | 2/2007 | Lang et al. | ...................... | 600/416 |
| 7,239,908 B1 | 7/2007 | Alexander et al. | ............ | 600/427 |
| 7,245,697 B2 | 7/2007 | Lang | ............................ | 378/54 |
| 7,283,857 B1 | 10/2007 | Fallon et al. | ..................... | 600/407 |
| 7,292,674 B2 | 11/2007 | Lang | ............................ | 378/54 |
| 7,379,529 B2 | 5/2008 | Lang | ............................ | 378/54 |
| 7,467,892 B2 | 12/2008 | Lang et al. | ...................... | 378/207 |
| 7,486,919 B2 | 2/2009 | Furuya | ........................... | 399/313 |
| 7,545,964 B2 | 6/2009 | Lang et al. | ...................... | 382/128 |
| 7,580,504 B2 | 8/2009 | Lang et al. | ....................... | 378/56 |
| 7,636,459 B2 | 12/2009 | Dore et al. | ...................... | 382/128 |
| 7,660,453 B2 | 2/2010 | Lang | ............................ | 382/132 |
| 7,664,298 B2 | 2/2010 | Lang et al. | ...................... | 382/128 |
| 7,676,023 B2 | 3/2010 | Lang et al. | ....................... | 378/54 |
| 7,840,247 B2 | 11/2010 | Liew et al. | ...................... | 600/407 |
| 7,848,558 B2 | 12/2010 | Giger et al. | ..................... | 382/132 |
| 7,995,822 B2 | 8/2011 | Lang et al. | ...................... | 382/128 |
| 8,000,441 B2 | 8/2011 | Lang et al. | ....................... | 378/56 |
| 8,000,766 B2 | 8/2011 | Lang et al. | ..................... | 600/407 |
| 8,031,836 B2 | 10/2011 | Lang et al. | ....................... | 378/54 |
| 8,068,580 B2 | 11/2011 | Lang et al. | ....................... | 378/54 |
| 8,073,521 B2 | 12/2011 | Liew et al. | ...................... | 600/407 |
| 8,260,018 B2 | 9/2012 | Lang et al. | ...................... | 382/128 |
| 8,290,564 B2 | 10/2012 | Lang et al. | ..................... | 600/407 |

(56) References Cited

U.S. PATENT DOCUMENTS

| | | | |
|---|---|---|---|
| 8,377,016 B2 | 2/2013 | Argenta et al. | 604/305 |
| 8,588,365 B2 | 11/2013 | Lang et al. | 378/56 |
| 8,600,124 B2 | 12/2013 | Arnaud et al. | 382/128 |
| 8,617,175 B2 | 12/2013 | Park et al. | 606/89 |
| 8,625,874 B2 | 1/2014 | Lang et al. | 382/132 |
| 8,639,009 B2 | 1/2014 | Lang et al. | 382/132 |
| 8,649,481 B2 | 2/2014 | Lang et al. | 378/54 |
| 2001/0020240 A1 | 9/2001 | Classen | 707/104.1 |
| 2002/0082779 A1 | 6/2002 | Ascenzi | 702/19 |
| 2002/0087274 A1 | 7/2002 | Alexander et al. | 702/19 |
| 2002/0114425 A1 | 8/2002 | Lang et al. | 378/56 |
| 2002/0159567 A1 | 10/2002 | Sako et al. | 378/117 |
| 2002/0186818 A1 | 12/2002 | Arnaud et al. | 378/165 |
| 2002/0188297 A1 | 12/2002 | Dakin et al. | 606/72 |
| 2002/0194019 A1 | 12/2002 | Evertsz | 705/2 |
| 2002/0196966 A1 | 12/2002 | Jiang et al. | 382/132 |
| 2003/0015208 A1 | 1/2003 | Lang et al. | 128/922 |
| 2003/0133601 A1 | 7/2003 | Giger et al. | 382/128 |
| 2003/0158159 A1 | 8/2003 | Schwartz | 514/170 |
| 2003/0175680 A1 | 9/2003 | Allard et al. | 435/4 |
| 2003/0198316 A1 | 10/2003 | Dewaele et al. | 378/54 |
| 2004/0009459 A1 | 1/2004 | Anderson et al. | 434/262 |
| 2004/0106868 A1* | 6/2004 | Liew et al. | 600/442 |
| 2004/0114789 A1 | 6/2004 | Saha et al. | 382/128 |
| 2004/0204760 A1 | 10/2004 | Fitz et al. | 623/14.12 |
| 2004/0247074 A1 | 12/2004 | Langton | 378/54 |
| 2004/0254439 A1 | 12/2004 | Fowkes et al. | 600/407 |
| 2005/0015002 A1 | 1/2005 | Dixon et al. | 600/407 |
| 2005/0037515 A1 | 2/2005 | Nicholson et al. | 436/173 |
| 2005/0059887 A1 | 3/2005 | Mostafavi et al. | 600/427 |
| 2005/0148860 A1 | 7/2005 | Liew et al. | 600/410 |
| 2005/0203384 A1 | 9/2005 | Sati et al. | 600/426 |
| 2005/0240096 A1 | 10/2005 | Ackerman et al. | 600/410 |
| 2006/0062442 A1 | 3/2006 | Arnaud et al. | 382/128 |
| 2007/0047794 A1 | 3/2007 | Lang et al. | 382/132 |
| 2007/0156066 A1 | 7/2007 | McGinley et al. | 600/587 |
| 2007/0274442 A1 | 11/2007 | Gregory et al. | 378/54 |
| 2008/0031412 A1 | 2/2008 | Lang et al. | 378/54 |
| 2008/0058613 A1 | 3/2008 | Lang et al. | 600/300 |
| 2008/0097794 A1 | 4/2008 | Arnaud et al. | 705/3 |
| 2008/0219412 A1 | 9/2008 | Lang | 378/207 |
| 2009/0207970 A1 | 8/2009 | Lang | 378/38 |
| 2009/0225958 A1 | 9/2009 | Lang | 378/207 |
| 2010/0014636 A1 | 1/2010 | Lang et al. | 378/56 |
| 2010/0098212 A1 | 4/2010 | Lang | 378/54 |
| 2010/0130832 A1 | 5/2010 | Lang et al. | 600/300 |
| 2010/0197639 A1 | 8/2010 | Lang et al. | 514/143 |
| 2010/0210972 A1 | 8/2010 | Vargas-Voracek | 600/587 |
| 2011/0036360 A1 | 2/2011 | Lang et al. | 128/898 |
| 2011/0040168 A1 | 2/2011 | Arnaud et al. | 600/407 |
| 2011/0105885 A1 | 5/2011 | Liew et al. | 600/410 |
| 2012/0027283 A1 | 2/2012 | Lang et al. | 382/132 |
| 2012/0063568 A1 | 3/2012 | Lang et al. | 378/56 |
| 2012/0072119 A1 | 3/2012 | Lang et al. | 702/19 |
| 2012/0087468 A1 | 4/2012 | Lang et al. | 378/56 |
| 2013/0039592 A1 | 2/2013 | Lang et al. | 382/232 |
| 2013/0113802 A1 | 5/2013 | Weersink et al. | 345/427 |
| 2013/0195325 A1 | 8/2013 | Lang et al. | 382/128 |

FOREIGN PATENT DOCUMENTS

| | | | | |
|---|---|---|---|---|
| EP | 0314506 | 5/1989 | | A61B 6/14 |
| EP | 0797952 | 10/1997 | | A61B 8/08 |
| EP | 0570936 | 8/2000 | | A61B 8/08 |
| EP | 0678191 | 2/2001 | | G01D 18/00 |
| EP | 1230896 | 8/2002 | | A61B 6/14 |
| EP | 1283492 | 2/2003 | | G06F 19/00 |
| EP | 1349098 | 10/2003 | | G06F 19/00 |
| EP | 1357480 | 10/2003 | | G06F 17/00 |
| EP | 1424650 | 6/2004 | | G06F 19/00 |
| EP | 1598778 | 11/2005 | | G06T 3/40 |
| EP | 1069395 | 7/2006 | | G01B 3/10 |
| GB | 2023920 | 1/1980 | | H01J 35/14 |
| JP | 62 266053 | 11/1987 | | A61C 19/04 |
| JP | 05 099829 | 4/1993 | | G01N 9/24 |
| JP | 08 186762 | 7/1996 | | H04N 5/325 |
| JP | 10 145396 | 5/1998 | | H04L 12/28 |
| JP | 10 262959 | 10/1998 | | A61B 6/00 |
| JP | 11 069136 | 3/1999 | | H04N 1/387 |
| JP | 11 112877 | 4/1999 | | H04N 5/325 |
| JP | 2002 045722 | 2/2000 | | B02C 18/42 |
| JP | 2000 126168 | 5/2000 | | A61B 6/00 |
| JP | 2000 139889 | 5/2000 | | A61B 6/00 |
| JP | 2003 230557 | 8/2003 | | A61B 6/00 |
| WO | WO 94/12855 | 6/1994 | | G01D 18/00 |
| WO | WO 95/14431 | 6/1995 | | A61B 5/103 |
| WO | WO 99/08597 | 2/1999 | | A61B 8/00 |
| WO | WO 99/45371 | 9/1999 | | G01N 23/06 |
| WO | WO 99/52331 | 10/1999 | | H05G 1/10 |
| WO | WO 00/33157 | 6/2000 | | |
| WO | WO 00/72216 | 11/2000 | | G06F 19/00 |
| WO | WO 01/38824 | 5/2001 | | G01B 15/02 |
| WO | WO 01/63488 | 8/2001 | | G06F 17/30 |
| WO | WO 01/65449 | 9/2001 | | G06F 17/60 |
| WO | WO 02/17789 | 3/2002 | | A61B 6/00 |
| WO | WO 02/22014 | 3/2002 | | A61B 5/055 |
| WO | WO 02/30283 | 4/2002 | | A61B 6/00 |
| WO | WO 02/096284 | 12/2002 | | A61B 5/00 |
| WO | WO 03/071934 | 9/2003 | | |
| WO | WO 03/073232 | 9/2003 | | |
| WO | WO 03/088085 | 10/2003 | | G06F 17/30 |
| WO | WO 2004/019256 | 3/2004 | | G06F 19/00 |
| WO | WO 2004/025541 | 3/2004 | | G06F 19/00 |
| WO | WO 2004/062495 | 7/2004 | | A61B 5/00 |
| WO | WO 2004/086972 | 10/2004 | | A61B 6/00 |
| WO | WO 2004/096048 | 11/2004 | | A61B 6/00 |
| WO | WO 2005/027732 | 3/2005 | | |
| WO | WO 2006/033712 | 3/2006 | | A61B 6/00 |
| WO | WO 2006/034018 | 3/2006 | | G06T 7/00 |
| WO | WO 2008/034101 | 3/2008 | | |
| WO | WO 99/45845 | 9/2009 | | A61B 8/00 |

OTHER PUBLICATIONS

Bauer et al., "Biochemical Markers of Bone Turnover and Prediction of Hip Bone Loss in Older Women: The Study of Osteoporotic Fractures," *Journal of Bone and Mineral Research*, vol. 14, pp. 1404-1410 (1999).

Beck et al., "Experimental Testing of a DEXA-Derived Curved Beam Model of the Proximal Femur," Journal of Orthopaedic Research, vol. 16, No. 3, pp. 394-398 (1998).

Black et al., "An Assessment Tool for Predicting Fracture Risk in Postmenopausal Women" *Osteoporosis International*, vol. 12, pp. 519-528 (2001).

Blake et al., "Active Contours; The Application of Techniques from Graphics, Vision, Control Theory and Statistics to Visual Tracking of Shapes in Motion," Title page and Table of Contents pages only, 6 pages (1999).

Burgkart et al., "Magnetic Resonance Imaging-Based Assessment of Cartilage Loss in Severe Osteoarthritis," Arthritis and Rheumatism, vol. 44, No. 9, pp. 2072-2077 (2001).

Bushberg et al., "The Essential Physics of Medical Imaging," Lipincott, Williams & Wilkins, Title page and Table of Contents pages only, 3 pages (1994).

Cann, "Quantitative CT for Determination of Bone Mineral Density: A Review," Radiology, vol. 166, No. 2, pp. 509-522 (1988).

Castleman, "Digital Image Processing," Prentice Hall, Title page and Table of Contents pages only, 9 pages (1996).

Cheal et al., "Role of Loads & Prosthesis Material Properties on the Mechanics of the Proximal Femur After Total Hip Arthroplasty," *J. Orthop. Res.*, vol. 10, No. 3, pp. 405-422 (1992).

Cootes et al., "Anatomical statistical models and their role in feature extraction," *The British Journal of Radiology*, Special Issue, 7 pages [S133-S139] (2004).

Cootes et al., "Statistical models of appearance for medical image analysis and computer vision," *Proc. SPIE Medical Imaging*, 14 pages, (2001).

Cootes, "An Introduction to Active Shape Models," *Image Processing and Analysis*, Ch. 7, pp. 1-26 (2000).

(56) References Cited

OTHER PUBLICATIONS

Cortet et al., "Bone Microarchitecture and Mechanical Resistance," *Joint Bone Spine*, vol. 68, pp. 297-305 (2001).
Crabtree et al., "Improving Risk Assessment: Hip Geometry, Bone Mineral Distribution and Bone Strength in Hip Fracture Cases and Controls. The EPOS Study," *Osteoporos Int*, vol. 13, pp. 48-54 (2002).
Crawley, "In Vivo Tissue Characterization Using Quantitative Computed Tomography: A Review," *Journal of Medical Engineering & Technology*, vol. 14, No. 6, pp. 233-242 (1990).
Cummings et al., "Bone Density at Various Sites for Prediction of Hip Fractures," *The Lancet*, vol. 341, pp. 72-75 (1993).
Davies et al., "A Minimum Description Length Approach to Statistical Shape Modeling," IEEE Transaction on Medical Imaging, vol. 21, No. 5, pp. 525-537 (2002).
Duryea et al., "New radiographic-based surrogate outcome measures for osteoarthritis of the knee," *Osteoarthritis and Cartilage*, vol. 11, pp. 102-110 (2003).
Duryea et al., "Trainable rule-based algorithm for the measurement of joint space width in digital radiographic images of the knee," *Medical Physics*, vol. 27, No. 3, pp. 580-591 (2000).
Eastell, "Treatment of Postmenopausal Osteoporosis," *New Engl. J. of Med.*, vol. 338, No. 11, pp. 736-746 (1988).
Engelman et al., "Impact of Geographic Barriers on the Utilization of Mammograms by Older Rural Women, " *Journal of the American Geriatrics Society*, vol. 50, No. 1, pp. 62-68 (2002).
Faulkner, "Bone Densitometry: Choosing the Proper Skeletal Site to Measure," *J. Clin. Densitometry*, vol. 1, No. 3, pp. 279-285 (1998).
Fleute et al., "Incorporating a statistically based shape model into a system for computer-assisted anterior cruciate ligament surgery," *Medical Image Analysis*, vol. 3, No. 3, pp. 209-222 (1999).
Fleute et al., "Statistical model registration for a C-arm CT system," Computer Science Department, The Johns Hopkins University, pp. 1667-1670 (2002).
Fleute et al., "Nonrigid 3-D/2-D Registration of Images Using Statistical Models," pp. 138-147 (1999).
Geraets et al., "A New Method for Automatic Recognition of the Radiographic Trabecular Pattern," *J. Bone and Min. Res.*, Department of Oral Radiology, Academic Center for Dentistry Amsterdam (ACTA), vol. 3, No. 3, pp. 227-233 (1990).
Gilliland et al., "Patterns of Mammography Use Among Hispanic, American Indian, and Non-Hispanic White Women in New Mexico, 1994-1997," *American Journal of Epidemiology*, vol. 152, No. 5, pp. 432-437 (2000).
Gluer et al., Peripheral Measurement Techniques for the Assessment of Osteoporosis, *Semin. Nucl. Med.*, vol. 27, No. 3, pp. 229-247 (1997).
Gluer, "Quantitative Ultrasound Techniques for the Assessment of Osteoporosis: Expert Agreement on Current Status," *J. Bone Miner. Res.*, vol. 12, No. 8, pp. 1280-1288 (1997).
Grisso et al., "Risk Factors for Falls as a Cause of Hip Fracture in Women. The Northeast Hip Fracture Study Group," *N. Engl. J. Med.*, (Abstract Page Only), 1 page, vol. 324, No. 19 (1991).
Gudmundsdottir et al., "Vertebral Bone Density in Icelandic Women Using Quantitative Computed Tomography Without an External Reference Phantom," *Osteoporosis Int.*, vol. 3, pp. 84-89 (1993).
Hayes et al., "Biomechanics of Cortical and Trabecular Bone: Implications for Assessment of Fracture Risk," *Basic Orthopaedic Biomechanics*, 2nd Ed., Ch. 3, pp. 69-111, Lippincott-Raven, publishers (1997).
Hayes et al., "Biomechanics of Fracture Risk Prediction of the Hip and Spine by Quantitative Computed Tomography," *Radiologic Clinics of North America*, vol. 29, No. 1, pp. 1-18 (1991).
Hayes et al., "Impact Near the Hip Dominates Fracture Risk in Elderly Nursing Home Residents Who Fall," *Calcif. Tissue Int.* (Abstract Page Only), 1 page, vol. 52, No. 3 (1993).
Hedström et al., "Biochemical Bone Markers and Bone Density in Hip Fracture Patients," *Acta Orthop. Scand.*, vol. 71, No. 4, pp. 409-413 (2000).
Hologic, Classic DXA Technology for the Office-based Practice, QDR-4000 Clinical Bone Densitometer, 8 pages, date unknown.
Horn, "Closed-form solution of absolute orientation using unit quaternions," *J. Opt. Soc. of Am. A*, vol. 4, No. 4, pp. 629-642 (1987).
Hosking et al., "Prevention of Bone Loss with Alendronate in Postmenopausal Women Under 60 Years of Age," *N. Engl. J. Med.*, vol. 338, No. 8, pp. 485-492 (1998).
Ikuta et al., "Quantitative Analysis Using the Star Volume Method Applied to Skeleton Patterns Extracted with a Morphological Filter," *Journal of Bone and Mineral Metabolism*, vol. 18, pp. 271-277 (2000).
Jacobs et al., "Long-term Bone Mass Evaluation of Mandible and Lumbar Spine in a Group of Women Receiving Hormone Replacement Therapy," *European Journal Oral Sciences*, vol. 104, pp. 10-16 (1996).
Jazieh et al., "Mammography Utilization Pattern Throughout the State of Arkansas: A Challenge for the Future," *Journal of Community Health*, vol. 26, No. 4, pp. 249-255 (2001).
Jeffcoat et al., "Post-menopausal bone loss and its relationship to oral bone loss", *Periodontology*, vol. 23, pp. 94-102 (2000).
Klose, "Teleradiology—A Model for Remote Consultation," *Electromedica*, vol. 66, No. 1, pp. 37-41 (1998).
Kumasaka et al., "Initial Investigation of Mathematical Morphology for the Digital Extraction of the Skeletal Characteristics of Trabecular Bone," *Dept. of Oral Surgery and Oral and Maxillofacial Radiology*, Kanagawa Dental College, Japan, pp. 161-168 (1996).
Lam et al., "X-Ray Diagnosis: A Physician's Approach," Title/Copyright pages and Index pages only, 4 pages, Springer-Verlag, publisher (ISBN 9813083247) (1998).
Lang et al., "Osteoporosis—Current Techniques and Recent Developments in Quantitative Bone Densitometry" *Radiologic Clinics of North America*, vol. 29, No. 1, pp. 49-76 (1991).
Majumdar et al., Correlation of Trabecular Bone Structure with Age, Bone Mineral Density, and Osteoporotic Status: In Vivo Studies in the Distal Radius Using High Resolution Magnetic Resonance Imaging, Journal of Bone and Mineral Research, vol. 12, No. 1, pp. 111-118, 1997.
Marshall et al., "Meta-Analysis of How Well Measures of Bone Mineral Density Predict Occurrence of Osteoporotic Fractures," *Br. Med. J.*, vol. 312, pp. 1254-1259 (1996).
Metrabio Website, "QUS-2 Calcaneal Ultrasonometer," What's New: Ultrasound, Retrieved from the Internet—http://www.metrabio.com/html/_prods/L3-ultrasound-r.ht, 2 pages (2001).
Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).
Njeh et al., "The Role of Ultrasound in the Assessment of Osteoporosis: A Review," *Osteoporosis Int.*, vol. 7, pp. 7-22 (1997).
Njeh et al., "Quantitative Ultrasound: Assessment of Osteoporosis and Bone Status," Title page and Table of Contents pages only, 4 pages (1999).
Ouyang et al., "Morphometric Texture Analysis of Spinal Trabecular Bone Structure Assessed Using Orthogonal Radiographic Projections," *Med. Phys.*, vol. 25, No. 10, pp. 2037-2045 (1998).
Patel et al., "Radiation Dose to the Patient and Operator from a Peripheral Dual X-Ray Absorptiometry System," *Journal of Clinical Densitometry*, vol. 2, No. 4, pp. 397-401 (1999).
Pharoah, "X-Ray Film, Intensifying Screens, and Grids," Ch. 4, Section 4: Imaging Principles and Techniques, Oral Radiology, 4th ed., pp. 68-76 (2000).
Pinilla et al., "Impact Direction from a Fall Influences the Failure Load of the Proximal Femur as Much as Age-Related Bone Loss," *Calcified Tissue International*, vol. 58, pp. 231-235 (1996).
Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).
Russ, "The Image Processing Handbook," 3rd Edition, North Carolina State Univ., Chapter 7: Processing Binary Images, pp. 494-501 (1998).

(56) References Cited

OTHER PUBLICATIONS

Ruttiman et al., "Fractal Dimension from Radiographs of Peridontal Alveolar Bone: A Possible Diagnostic Indicator of Osteoporosis," *Oral Surg, Oral Med, Oral Pathol.*, vol. 74, No. 1, pp. 98-110 (1992).

Sandler et al., "An Analysis of the Effect of Lower Extremity Strength on Impact Severity During a Backward Fall," *Journal of Biomechanical Engineering*, vol. 123, pp. 590-598 (2001).

Shrout et al., "Comparison of Morphological Measurements Extracted from Digitized Dental Radiographs with Lumbar and Femoral Bone Mineral Density Measurements in Postmenopausal Women," *J. Periondontal*, vol. 71, No. 3, pp. 335-340 (2000).

Slone et al., "Body CT: A Practical Approach," Title page and Table of Contents pages only, 4 pages, McGraw-Hill, publisher (ISBN 007058219) (1999).

Southard et al., "Quantitative Features of Digitized Radiographic Bone Profiles," *Oral Surgery, Oral Medicine, and Oral Pathology*, vol. 73, No. 6, pp. 751-759 (1992).

Southard et al., "The Relationship Between the Density of the Alveolar Processes and that of Post-Cranial Bone," *J. Dent. Res.*, vol. 79, No. 4, pp. 964-969 (2000).

Stout et al., "X-Ray Structure Determination: A Practical Guide," 2nd Ed., Title page and Table of Contents pages only, 4 pages, John Wiley & Sons, publisher (ISBN 0471607118) (1989).

Svendsen et al., "Impact of Soft Tissue on In-Vivo Accuracy of Bone Mineral Measurements in the Spine, Hip, and Forearm: A Human Cadaver Study," *J. Bone Miner. Res.*, vol. 10, No. 6, pp. 868-873 (1995).

Tothill et al., "Errors due to Non-Uniform Distribution of Fat in Dual X-Ray Absorptiometry of the Lumbar Spine," *Br. J. Radiol.*, vol. 65, pp. 807-813 (1992).

Van den Kroonenberg et al., "Dynamic Models for Sideways Falls from Standing Height," *Journal of Biomechanical Engineering*, vol. 117, pp. 309-318 (1995).

Verhoeven et al., "Densitometric Measurement of the Mandible: Accuracy and Validity of Intraoral Versus Extraoral Radiographic Techniques in an In Vitro Study," *Clin. Oral Impl. Res.*, vol. 9, pp. 333-342 (1998).

White et al., "Alterations of the Trabecular Pattern in the Jaws of Patients with Osteoporosis," *Oral Surg., Oral Med., Oral Pathol., Oral Radiol., and Endod.*, vol. 88, pp. 628-635 (1999).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

\* cited by examiner

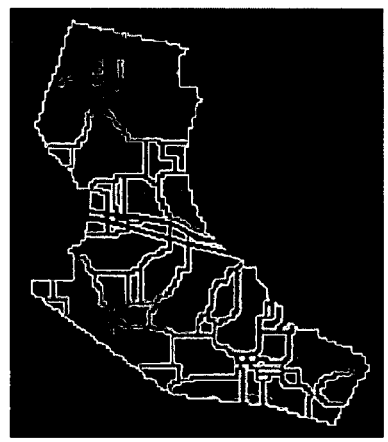
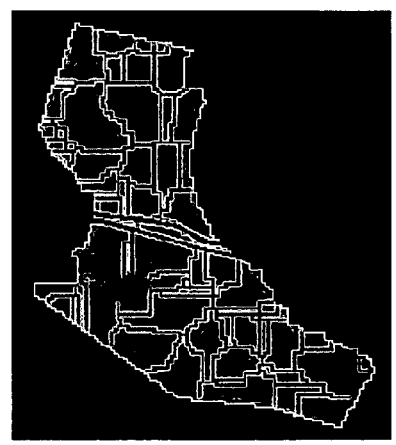
FIG. 6

SYSTEM AND METHOD OF PREDICTING FUTURE FRACTURES

CROSS-REFERENCE TO RELATED APPLICATIONS

This patent application is a continuation of U.S. patent application Ser. No. 11/228,126, filed Sep. 16, 2005, now U.S. Pat. No. 8,600,124, which claims the benefit of U.S. Patent Application Ser. No. 60/610,447, filed Sep. 16, 2004, the disclosures of which are incorporated by reference herein in its entireties.

BACKGROUND OF THE INVENTION

1. Field of the Invention

This invention relates to using imaging methods for predicting fracture risk and/or location based on radiographs.

2. Description of the Related Art

Osteoporosis is among the most common conditions to affect the musculoskeletal system, as well as a frequent cause of locomotor pain and disability. Osteoporosis can occur in both human and animal subjects (e.g. horses). Osteoporosis (OP) occurs in a substantial portion of the human population over the age of fifty. The National Osteoporosis Foundation estimates that as many as 44 million Americans are affected by osteoporosis and low bone mass. In 1997 the estimated cost for osteoporosis related fractures was $13 billion. That figure increased to $17 billion in 2002 and is projected to increase to $210-240 billion by 2040. Currently it is expected that one in two women over the age of 50 will suffer an osteoporosis-related fracture.

Imaging techniques are important diagnostic tools, particularly for bone related conditions such as osteoporosis. Currently available techniques for the noninvasive assessment of the skeleton for the diagnosis of osteoporosis or the evaluation of an increased risk of fracture include dual x-ray absorptiometry (DXA) (Eastell et al. (1998) *New Engl J. Med* 338:736-746); quantitative computed tomography (QCT) (Cann (1988) *Radiology* 166:509-522); peripheral DXA (pDXA) (Patel et al. (1999) *J Clin Densitom* 2:397-401); peripheral QCT (pQCT) (Gluer et al. (1997) *Semin Nucl Med* 27:229-247); x-ray image absorptiometry (RA) (Gluer et al. (1997) *Semin Nucl Med* 27:229-247; and U.S. Pat. No. 6,246,745); and quantitative ultrasound (QUS) (Njeh et al. "*Quantitative Ultrasound: Assessment of Osteoporosis and Bone Status*", 1999, Martin-Dunitz, London England; WO 9945845; WO 99/08597; and U.S. Pat. No. 6,077,224 which is incorporated herein by reference in its entirety).

DXA of the spine and hip has established itself as the most widely used method of measuring bone mineral density (BMD). Tothill, P. and D. W. Pye, (1992) *Br J Radiol* 65:807-813. The fundamental principle behind DXA is the measurement of the transmission through the body of x-rays of 2 different photon energy levels. Because of the dependence of the attenuation coefficient on the atomic number and photon energy, measurement of the transmission factors at 2 energy levels enables the area densities (i.e., the mass per unit projected area) of 2 different types of tissue to be inferred. In DXA scans, these are taken to be bone mineral (hydroxyapatite) and soft tissue, respectively. However, it is widely recognized that the accuracy of DXA scans is limited by the variable composition of soft tissue. Because of its higher hydrogen content, the attenuation coefficient of fat is different from that of lean tissue. Differences in the soft tissue composition in the path of the x-ray beam through bone compared with the adjacent soft tissue reference area cause errors in the BMD measurements, according to the results of several studies. Tothill, P. and D. W. Pye, (1992) *Br J Radiol,* 65:807-813; Svendsen, O. L., et al., (1995) *J Bone Min Res* 10:868-873. Moreover, DXA systems are large and expensive, ranging in price between $75,000 and $150,000.

Quantitative computed tomography (QCT) is usually applied to measure the trabecular bone in the vertebral bodies. Cann (1988) *Radiology* 166:509-522. QCT studies are generally performed using a single kV setting (single-energy QCT), when the principal source of error is the variable composition of the bone marrow. However, a dual-kV scan (dual-energy QCT) is also possible. This reduces the accuracy errors but at the price of poorer precision and higher radiation dose. Like DXA, however, QCT are very expensive and the use of such equipment is currently limited to few research centers.

Quantitative ultrasound (QUS) is a technique for measuring the peripheral skeleton. Njeh et al. (1997) *Osteoporosis Int* 7:7-22; and Njeh et al., *Quantitative Ultrasound: Assessment of Osteoporosis and Bone Status,* 1999, Martin Dunitz, London, England. There is a wide variety of equipment available, with most devices using the heel as the measurement site. A sonographic pulse passing through bone is strongly attenuated as the signal is scattered and absorbed by trabeculae. Attenuation increases linearly with frequency, and the slope of the relationship is referred to as broadband ultrasonic attenuation (BUA; units: dB/MHz). BUA is reduced in patients with osteoporosis because there are fewer trabeculae in the calcaneus to attenuate the signal. In addition to BUA, most QUS systems also measure the speed of sound (SOS) in the heel by dividing the distance between the sonographic transducers by the propagation time (units: m/s). SOS values are reduced in patients with osteoporosis because with the loss of mineralized bone, the elastic modulus of the bone is decreased. There remain, however, several limitations to QUS measurements. The success of QUS in predicting fracture risk in younger patients remains uncertain. Another difficulty with QUS measurements is that they are not readily encompassed within the WHO definitions of osteoporosis and osteopenia. Moreover, no intervention thresholds have been developed. Thus, measurements cannot be used for therapeutic decision-making.

There are also several technical limitations to QUS. Many devices use a foot support that positions the patient's heel between fixed transducers. Thus, the measurement site is not readily adapted to different sizes and shapes of the calcaneus, and the exact anatomic site of the measurement varies from patient to patient. It is generally agreed that the relatively poor precision of QUS measurements makes most devices unsuitable for monitoring patients' response to treatment. Gluer (1997) *J Bone Min Res* 12:1280-1288.

Radiographic absorptiometry (RA) is a technique that was developed many years ago for assessing bone density in the hand, but the technique has recently attracted renewed interest. Gluer et al. (1997) *Semin Nucl Med* 27:229-247. With this technique, BMD is measured in the phalanges.

Furthermore, current methods and devices do not generally take into account bone structure analyses. See, e.g., Ruttimann et al. (1992) *Oral Surg Oral Med Oral Pathol* 74:98-110; Southard & Southard (1992) *Oral Surg Oral Med Oral Pathol* 73:751-9; White & Rudolph, (1999) *Oral Surg Oral Med Oral Pathol Oral Radiol Endod* 88:628-35.

BMD does not accurately predict the presence of osteoporotic fracture. See, e.g., Riggs et al. (1982) *J Clin Invest* 70:716-723; Krolner, B. and S. P. Nielsen (1982) *Clin Sci.* 62:329-336; Ott et al. (1987) *J Bone Miner Res,* 2:201-210; and Pacifici et al. (1987) *J Clin Endocrinol Metab,*

64:209-214. While BMD is correlated with long-term fracture risk in population based studies (Kains (1994) *Osteoporosis Int* 4:368-381), it cannot take into account factors that vary from patient to patient and that are major determinants of individual failure load and resultant fracture (Hayes, W. C. and M. L. Bouxsein, *Biomechanics of cortical and trabecular bone: Implications for assessment of fracture risk*, in *Basic Orthopaedic Biomechanics*, V. C. Mow and W. C. Hayes, Editors, 1997, Lippincott-Raven Publishers: Philadelphia, p. 69-111; Kroonenberg et al. (1995) *J Biomech Eng.* 117(3):309-318; Kroonenberg et al. (1996) *Biomechanics* 29(6):807-811; and Robinovitch et al. (1991) *J Biomech Eng.* 113:366-374). These factors include bone architecture and structure, bone morphology, and biomechanical loading and impact load. Indeed, patients receiving osteoclast inhibiting, anti-resorptive drugs show remarkable reductions in incident osteoporotic fractures by 60-65% but only small changes in BMD on the order of 4.0-4.5% (Reginster et al. (2000) *Osteoporosis Int.*,11(1):83-91; and Harris et al. (1999) *JAMA* 14:1344-1352), strongly indicating a significant discrepancy between clinical outcomes and BMD measurements of bone health.

Thus, there remains a need for compositions and methods for predicting fracture risk.

SUMMARY OF THE INVENTION

The invention discloses a method for predicting a fracture by analyzing at least one bone structure parameter. The method comprises: obtaining an image of a part of skeleton of a patient; locating at least one region of interest on the image of the patient; extracting image data from the image of the patient; deriving at least one bone structure parameter from the image data of the patient; and predicting a fracture with the bone structure parameter of the patient. The bone structure parameter includes, but not limited to, bone micro-structure parameters and bone macro-structure parameters.

In certain aspects, described herein are methods of diagnosing, monitoring and/or predicting bone or articular disease (e.g., the risk of fracture) in a subject, the method comprises the steps of: determining one or more micro-structural parameters, and/or one or more macro-structure parameters, possibly with other bone parameters, of a bone or a joint in the subject; and combining at least two of the parameters to predict the risk of bone or articular disease. The micro-structural and macro-structure parameters may be, for example, one or more of the measurements/parameters shown in Tables 1 and 2. In certain embodiments, one or more micro-structural parameters and one or more macro-structural parameters are combined. In other embodiments, one or more micro-structural parameters and one or more other bone parameters are combined. In further embodiments, one or more macro-structure parameters and one or more other parameters are combined. In still further embodiments, one or more macro-structural parameters, one or more micro-structural parameters and one or more other bone parameters are combined.

In any of the methods described herein, the comparing may comprise univariate, bivariate and/or multivariate statistical analysis of one or more of the parameters, including at least one bone structure parameter. In certain embodiments, the methods may further comprise comparing the parameters to data derived from a reference database of known disease parameters.

In any of the methods described herein, the parameters are determined from an image obtained from the subject. In certain embodiments, the image comprises one or more regions of bone (e.g., patella, femur, tibia, fibula, pelvis, spine, etc). The image may be automatically or manually divided into two or more regions of interest. Furthermore, in any of the methods described herein, the image may be, for example, an x-ray image, a CT scan, an MRI or the like and optionally includes one or more calibration phantoms.

In any of the methods described herein, the predicting includes performing univariate, bivariate or multivariate statistical analysis of the analyzed data and referencing the statistical analysis values to a fracture risk model. Fracture risk models can comprise, for example, data derived from a reference database of known fracture loads with their corresponding values of macro-anatomical, micro-anatomical parameters, and/or clinical risk factors.

In another aspect, the invention includes a method of determining the effect of a candidate agent on a subject's prognosis for musculoskeletal disease comprising: predicting a first risk of musculoskeletal disease in the subject according to any of the predictive methods described herein; administering a candidate agent to the subject; predicting a second risk of the musculoskeletal disease in the subject according to any of the predictive methods described herein; and comparing the first and second risks, thereby determining the effect of the candidate on the subject's prognosis for the disease. In any of these methods, the candidate agent can be administered to the subject in any modality, for example, by injection (intramuscular, subcutaneous, intravenous), by oral administration (e.g., ingestion), topical administration, mucosal administration or the like. Furthermore, the candidate agent may be a small molecule, a pharmaceutical, a biopharmaceutical, an agropharmaceuticals and/or combinations thereof. It is important to note that an effect on a subject's prognosis for musculoskeletal disease can occur in agents intended to have an effect, such as a therapeutic effect, on musculoskeletal disease as well as agents intended to primarily effect other tissues in the body but which have a secondary, or tangential, effect on musculoskeletal disease. Further, the agent can be evaluated for the ability to effect diseases such as the risk of bone fracture (e.g., osteoporotic fracture).

In other aspects, the invention includes a kit that is provided for aiding in the prediction of musculoskeletal disease (e.g., fracture risk). The kit typically comprises a software program that uses information obtained from an image to predict the risk or disease (e.g., fracture). The kit can also include a database of measurements for comparison purposes. Additionally, the kit can include a subset of a database of measurements for comparisons.

In any of these methods, systems or kits, additional steps can be provided. Such additional steps include, for example, enhancing image data.

Suitable subjects for these steps include for example mammals, humans and horses. Suitable anatomical regions of subjects include, for example, dental, spine, hip, knee and bone core x-rays.

A variety of systems can be employed to practice the inventions. Typically at least one of the steps of any of the methods is performed on a first computer. Although, it is possible to have an arrangement where at least one of the steps of the method is performed on a first computer and at least one of the steps of the method is performed on a second computer. In this scenario the first computer and the second computer are typically connected. Suitable connections include, for example, a peer to peer network, direct link, intranet, and internet.

It is important to note that any or all of the steps of the inventions disclosed can be repeated one or more times in series or in parallel with or without the repetition of other steps in the various methods. This includes, for example repeating the step of locating a region of interest, or obtaining image data.

Data can also be converted from 2D to 3D to 4D and back; or from 2D to 4D. Data conversion can occur at multiple points of processing the information. For example, data conversion can occur before or after pattern evaluation and/or analysis.

Any data obtained, extracted or generated under any of the methods can be compared to a database, a subset of a database, or data previously obtained, extracted or generated from the subject. For example, known fracture load can be determined for a variety of subjects and some or all of this database can be used to predict fracture risk by correlating one or more micro-structural parameters or macro-structural parameters (Tables 1 and 2) with data from a reference database of fracture load for age, sex, race, height and weight matched individuals.

In any of the methods described herein, the analysis can comprise using one or more computer programs (or units). Additionally, the analysis can comprise identifying one or more regions of interest (ROI) in the image, either prior to, concurrently or after analyzing the image, e.g. for information on bone structure. Bone structural information can be, for example, one or more of the parameters shown in Table 1 and Table 2. The various analyses can be performed concurrently or in series. Further, when using two or more indices each of the indices can be weighted equally or differently, or combinations thereof where more than two indices are employed. Additionally, any of these methods can also include analyzing the image for bone structure information using any of the methods described herein.

These and other embodiments of the subject invention will readily occur to those of skill in the art in light of the disclosure herein.

BRIEF DESCRIPTION OF THE DRAWINGS

FIG. 3A depicts correlation of 2D and 3D trabecular spacing. FIG. 3B depicts correlation of 2D trabecular perimeter/trabecular area with 3D bone surface/bone volume.

FIG. 4A depicts 2D trabecular perimeter/trabecular area v. fracture load. FIG. 4B depicts 2D trabecular separation vs. fracture load.

FIGS. 6A to 6D depict sliding window analysis maps for two different femora. The top maps (FIGS. 6A and 6B) depict area ratio analysis. The bottom maps (FIGS. 6C and 6D) depict trabecular perimeter analysis. Black lines show fracture lines from post-fracture x-rays for proximal and distal fragments. Red lines show results of watershed analysis of parameter maps. Color scale ranges from blue (low values) to red (high values).

DETAILED DESCRIPTION OF EMBODIMENTS

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

The practice of the present invention employs, unless otherwise indicated, methods of imaging and image processing within the skill of the art. Currently available imaging methods are explained fully in the literature. See, e.g., WO 02/22014; *X-Ray Structure Determination: A Practical Guide*, $2^{nd}$ Edition, editors Stout and Jensen, 1989, John Wiley & Sons, publisher; *Body CT: A Practical Approach*, editor Slone, 1999, McGraw-Hill publisher; *The Essential Physics of Medical Imaging*, editors Bushberg, Seibert, Leidholdt Jr & Boone, 2002, Lippincott, Williams & Wilkins; *X-ray Diagnosis: A Physician's Approach*, editor Lam, 1998 Springer-Verlag, publisher; *Dental Radiology: Understanding the X-Ray Image*, editor Laetitia Brocklebank 1997, Oxford University Press publisher; *Digital Image Processing*, editor Kenneth R. Castleman, 1996, Prentice Hall, publisher; *The Image Processing Handbook*, editor John C. Russ, $3^{th}$ Edition, 1998, CRC Press; and *Active Contours: The Application of Techniques from Graphics, Vision, Control Theory and Statistics to Visual Tracking of Shapes in Motion*, Editors Andrew Blake, Michael Isard, 1999 Springer Verlag. As will be appreciated by those of skill in the art, as the field of imaging continues to advance, methods of imaging currently employed can evolve over time. Thus, any imaging method or technique that is currently employed is appropriate for application of the teachings of this invention as well as techniques that can be developed in the future. A further detailed description of imaging methods is not provided in order to avoid obscuring the invention.

Figure 1:
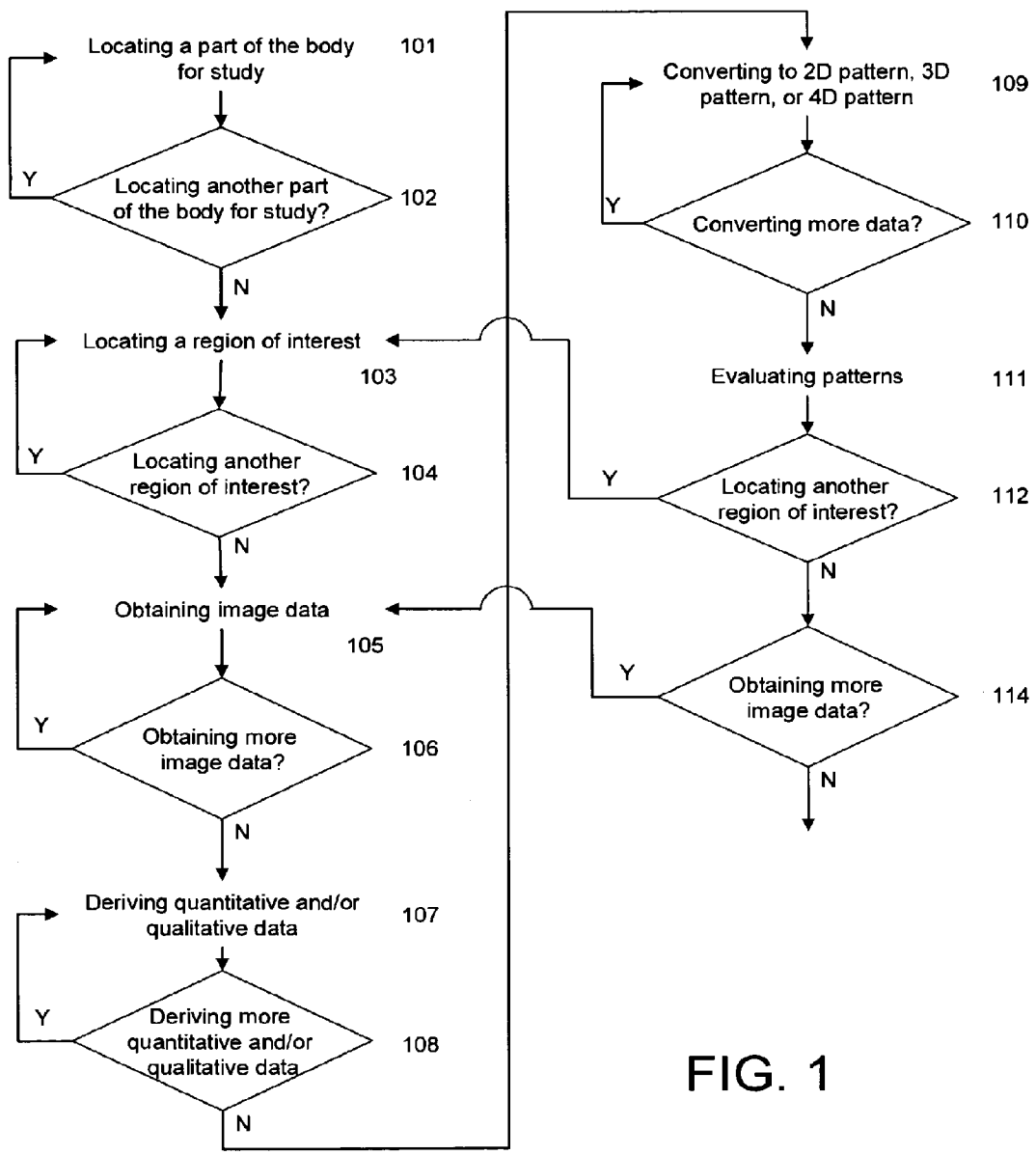
FIG. 1 shows a flowchart of a method for collecting quantitative and/or qualitative data according to one embodiment of the present invention.

FIG. 1 shows a method for collecting quantitative and/or qualitative data according to one embodiment of the present application. Step 101 is used to locate a part of the body of a subject, for example in a human body, for study. The part of the body located for study is the region of anatomical interest (RAI). In locating a part of the body for study, a determination is made to, for example, take an image or a series of images of the body at a particular location, e.g. hip, dental, spine, etc. Images include, for example, conventional x-ray images, x-ray tomosynthesis, ultrasound (including A-scan, B-scan and C-scan), computed tomography (CT scan), magnetic resonance imaging (MRI), optical coherence tomography, single photon emission tomography (SPECT), and positron emission tomography, or such other imaging tools that a person of skill in the art would find useful in practicing the invention. Once the image is taken, one or more regions of interest (ROI) can be manually and/or automatically located within the image at step 103. A skilled artisan would appreciate that algorithms can be used to automatically place regions of interest in a particular image. For instance, Example 1 below describes automatic placement of ROIs in femurs. Image data is extracted from the image at step 105. Finally, quantitative and/or qualitative data is extracted from the image data at step 107. The quantitative and/or qualitative data extracted from the image include at least one measurement about bone structure, such as those shown in Tables 1 and 2.

Each step of locating a part of the body for study 101, optionally locating a region of interest 103, obtaining image data 105, and deriving quantitative and/or qualitative data 107, can be repeated one or more times at step 102, 104, 106, or 108, respectively, as desired. Image data can be optionally enhanced by applying image processing techniques, such as noise filtering or diffusion filtering, to facilitate further analysis.

TABLE 1

Representative Parameters Measured with Quantitative and Qualitative Image Analysis Methods for Micro-structure

| PARAMETER | MEASUREMENTS |
|---|---|
| Measurements on extracted micro-structures | Trabecular contrast |
| | Standard deviation of background subtracted ROI |
| | Coefficient of Variation of ROI (Standard deviation/mean) |
| | (Trabecular equivalent thickness/Marrow equivalent thickness) |
| | Hough transform |
| | Trabecular area |
| | (Pixel count of extracted trabeculae) |
| | Trabecular area/Total area |
| | Trabecular perimeter |
| | (Count of trabecular pixels with marrow pixels in their neighborhood, proximity or vicinity) |
| | Trabecular distance transform |
| | (For each trabecular pixel, calculation of distance to closest marrow pixel) |
| | Marrow distance transform |
| | (For each marrow pixel, calculation of distance to closest trabecular pixel) |
| | Trabecular distance transform regional maximal values (mean, min., max, std. Dev). |
| | (Describes thickness and thickness variation of trabeculae) |
| | Marrow distance transform regional maximal values (mean, min., max, std. Dev) |
| | Star volume |
| | (Mean volume of all the parts of an object which can be seen unobscured from a random point inside the object in all possible directions) |
| | Trabecular Bone Pattern Factor |
| | (TBPf = (P1 − P2)/(A1 − A2) where P1 and A1 are the perimeter length and trabecular bone area before dilation and P2 and A2 corresponding values after a single pixel dilation, measure of connectivity) |
| Measurements on skeleton of extracted micro-structures | Connected skeleton count or Trees (T) |
| | Node count (N) |
| | Segment count (S) |
| | Node-to-node segment count (NN) |
| | Node-to-free-end segment count (NF) |
| | Node-to-node segment length (NNL) |
| | Node-to-free-end segment length (NFL) |
| | Free-end-to-free-end segment length (FFL) |
| | Node-to-node total struts length (NN.TSL) |
| | Free-end-to-free-ends total struts length(FF.TSL) |
| | Total struts length (TSL) |
| | FF.TSL/TSL |
| | NN.TSL/TSL |
| | Loop count (Lo) |
| | Loop area |
| | Mean distance transform values for each connected skeleton |
| | Mean distance transform values for each segment (Tb.Th) |
| | Mean distance transform values for each node-to-node segment (Tb.Th.NN) |

TABLE 1-continued

Representative Parameters Measured with
Quantitative and Qualitative Image Analysis Methods for Micro-structure

| PARAMETER | MEASUREMENTS |
|---|---|
| | Mean distance transform values for each node-to-free-end segment (Tb.Th.NF) |
| | Orientation (angle) of each segment |
| | Angle between segments |
| | Length-thickness ratios (NNL/Tb.Th.NN) and (NFL/Tb.Th.NF) |
| | Interconnectivity index (ICI) ICI = (N * NN)/(T * (NF + 1)) |
| Measurements on gray level images of micro-structures | Standard deviation of background subtracted ROI |
| | Coefficient of Variation of ROI (Standard deviation/mean) |
| | Fractal dimension |
| | Fourier spectral analysis |
| | (Mean transform coefficient absolute value and mean spatial first moment) |
| | Predominant orientation of spatial energy spectrum |
| | Watershed segmentation is applied to gray level images. Statistics of watershed segments are: |
| | Total area of segments |
| | Number of segments normalized by total area of segments |
| | Average area of segments |
| | Standard deviation of segment area |
| | Smallest segment area |
| | Largest segment area |

All micro-structural measurements can be applied in a direction-sensitive fashion or only on selected structures. For example, they can be applied to selected structures that are oriented parallel or perpendicular to stress lines. The techniques can also be used to measure only horizontal or vertical structures.

As will be appreciated by those of skill in the art, the parameters and measurements shown in the tables are provided for illustration purposes only. It will be apparent that the terms micro-structural parameters, micro-architecture, micro-anatomic structure, micro-structural and trabecular architecture may be used interchangeably. Furthermore, the terms macro-structural parameters, macro-structure, macro-anatomic parameters, macro-anatomic structure, macro-anatomy, macro-architecture and bone geometry may be used interchangeably. In addition, other parameters and measurements, ratios, derived values or indices can be used to extract quantitative and/or qualitative information about the ROI without departing from the scope of the invention. Additionally, where multiple ROI or multiple derivatives of data are used, the parameter measured can be the same parameter or a different parameter without departing from the scope of the invention. Additionally, data from different ROIs can be combined or compared as desired. Additional measurements can be performed that are selected based on the anatomical structure to be studied as described below. For instance, biomechanical aspects of the joint can also be evaluated. For example, the product of the average trabecular-computed tomography number and the total cross-sectional area of the sub-capital, basicervical or intertrochanteric regions can be determined, as it has been shown to correlate highly with failure loads. See, e.g., Lotz et al. (1990) *J. Bone Joint Surg. Am.* 72:689-700; Courtney et al. (1995) *J. Bone Joint Surg. Am.* 77(3):387-395; Pinilla et al. (1996) *Calcif Tissue Int.* 58:231-235.

Once the quantitative and/or qualitative data is extracted from the image, it can be manipulated to assess the severity of the disease and to determine disease staging (e.g., mild, moderate, severe or a numerical value or index). The information can also be used to monitor progression of the disease and/or the efficacy of any interventional steps that have been taken. Finally, the information can be used to predict the progression of the disease or to randomize patient groups in clinical trials.

Figure 2:
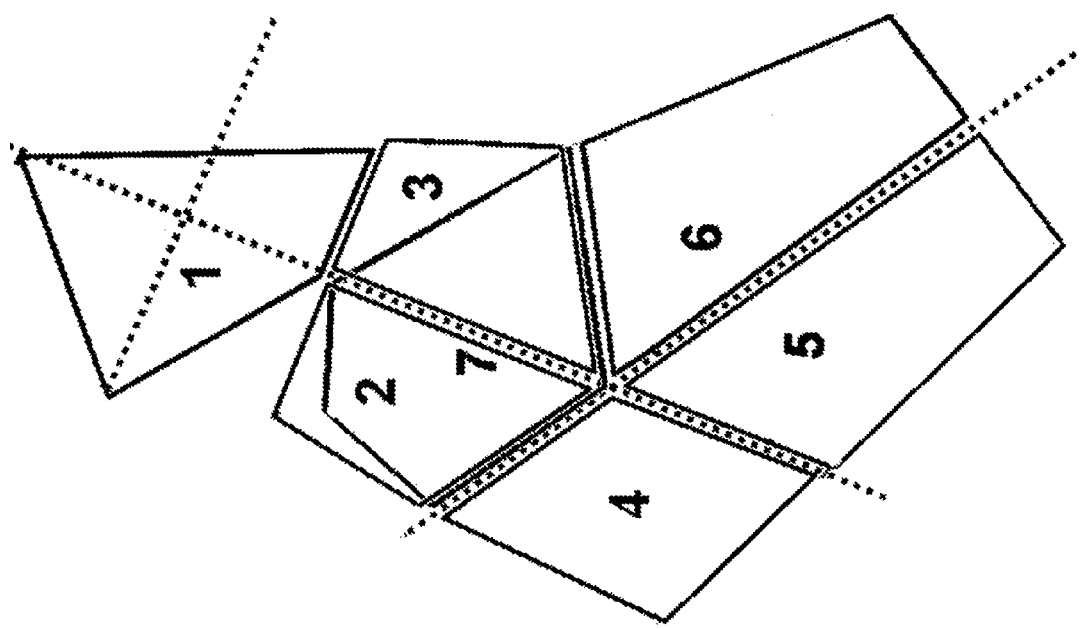
FIG. 2 depicts exemplary regions of interest (ROIs), as analyzed in Example 1 of the present invention.

After an image of an RAI is taken, one or more regions of interest can be identified within the image at step 103. The ROI can take up the entire image, or nearly the entire image. Alternatively, more than one ROI can be identified in an image, as shown in FIG. 2. One or more of the ROI may overlap or abut. As will be appreciated by a person of skill in the art, the number of ROI identified in an image is not limited to the seven depicted in FIG. 2. As also will be appreciated by those of skill in the art, where multiple ROI are used, any or all of the ROI can be organized such that it does not overlap, it abuts without overlapping, it overlaps partially, it overlaps completely (for example where a first ROI is located completely within a second identified ROI), and combinations thereof. Further the number of ROI per image can range from one ($ROI_1$) to n ($ROI_n$) where n is the number of ROI to be analyzed.

Bone structure analyses, possibly together with bone density, and/or biomechanical (e.g. derived using finite element modeling) analyses, can be applied within a region of predefined size and shape and position. This region of interest can also be referred to as a "window". Processing can be applied repeatedly by moving the window to different positions of the image. For example, a field of sampling points can be generated and the analysis performed at these points. The results of the analyses for each parameter can be stored in a matrix space, e.g., where its position corresponds to the position of the sampling point where the analysis occurred, thereby forming a map of the spatial distribution of the parameter (a parameter map). The sampling field can have regular intervals or irregular intervals with varying density across the image. The window can have variable size and shape, for example to account for different patient size or anatomy.

In another embodiment, rather than a fixed ROI (e.g., FIG. 3), the image may be overlaid with a regular grid, for example, a region of interest of a fixed size (e.g., of any shape) may be placed at each grid node, and parameters are evaluated within the boundaries of the ROI at each position. This results in a value for each bone parameter at each grid node, which can be displayed in a color-coded map of the proximal femur for each parameter.

The amount of overlap between the windows can be determined, for example, using the interval or density of the sampling points (and resolution of the parameter maps). Thus, the density of sampling points is set higher in regions where higher resolution is desired and set lower where moderate resolution is sufficient, in order to improve processing efficiency. The size and shape of the window would determine the local specificity of the parameter. Window size is preferably set such that it encloses most of the structure being measured. Oversized windows are generally avoided to help ensure that local specificity is not lost.

The shape of the window can be varied to have the same orientation and/or geometry of the local structure being measured to minimize the amount of structure clipping and to maximize local specificity. Thus, both 2D and/or 3D windows can be used, as well as combinations thereof, depending on the nature of the image and data to be acquired.

In another embodiment, bone structure analysis, possibly together with bone density and/or biomechanical (e.g. derived using finite element modeling) analyses, can be applied within a region of predefined size and shape and position. The region is generally selected to include most, or all, of the anatomic region under investigation and, preferably, the parameters can be assessed on a pixel-by-pixel basis (e.g., in the case of 2D or 3D images) or a voxel-by-voxel basis in the case of cross-sectional or volumetric images (e.g., 3D images obtained using MR and/or CT). Alternatively, the analysis can be applied to clusters of pixels or voxels wherein the size of the clusters is typically selected to represent a compromise between spatial resolution and processing speed. Each type of analysis can yield a parameter map.

Parameter maps can be based on measurement of one or more parameters in the image or window; however, parameter maps can also be derived using statistical methods. In one embodiment, such statistical comparisons can include comparison of data to a reference population, e.g. using a z-score or a T-score. Thus, parameter maps can include a display of z-scores or T-scores.

Additional measurements relating to the site to be measured can also be taken. For example, measurements can be directed to dental, spine, hip, knee or bone cores. Examples of suitable site specific measurements are shown in Table 2.

TABLE 2

| Common and site specific measurements of bone macro-structure parameters | |
|---|---|
| Measurements on macro-structures common to dental, spine, hip, knee or bone cores images | The following parameters are derived from the extracted macro-structures:<br>Calibrated density of extracted structures<br>Calibrated density of background<br>Average intensity of extracted structures<br>Average intensity of background (area other than extracted structures)<br>Structural contrast (average intensity of extracted structures/average intensity of background)<br>Calibrated structural contrast (calibrated density extracted structures/calibrated density of background)<br>Total area of extracted structures<br>Bone pattern factor; measures concavity and convexity of structures<br>Average length of structures (units of connected segments)<br>Maximum length of structures<br>Average thickness of structures<br>Maximum thickness of structures<br>Regional maximum thickness of structures<br>Standard deviation of thickness along structures<br>Average orientation angle of structure segmentss<br>Structure segment tortuosity; a measure of straightness<br>Structure segment solidity; another measure of straightness |
| Parameters specific to hip images | Shaft angle<br>Neck angle<br>Average and minimum diameter of femur neck<br>Hip axis length<br>CCD (caput-collum-diaphysis) angle<br>Width of trochanteric region<br>Largest cross-section of femur head<br>Standard deviation of cortical bone thickness within ROI<br>Minimum, maximum, mean and median thickness of cortical bone within ROI<br>Hip joint space width |
| Parameters specific to spine images | Superior endplate cortical thickness (anterior, center, posterior)<br>Inferior endplate cortical thickness (anterior, center, posterior)<br>Anterior vertebral wall cortical thickness (superior, center, inferior)<br>Posterior vertebral wall cortical thickness (superior, center, inferior)<br>Superior aspect of pedicle cortical thickness<br>inferior aspect of pedicle cortical thickness<br>Vertebral height (anterior, center, posterior)<br>Vertebral diameter (superior, center, inferior),<br>Pedicle thickness (supero-inferior direction).<br>Maximum vertebral height<br>Minimum vertebral height<br>Average vertebral height<br>Anterior vertebral height<br>Medial vertebral height |

TABLE 2-continued

Common and site specific measurements of bone macro-structure parameters

| | |
|---|---|
| | Posterior vertebral height |
| | Maximum inter-vertebral height |
| | Minimum inter-vertebral height |
| | Average inter-vertebral height |
| Parameters specific to knee images | Average medial joint space width |
| | Minimum medial joint space width |
| | Maximum medial joint space width |
| | Average lateral joint space width |
| | Minimum lateral joint space width |
| | Maximum lateral joint space width |

As will be appreciated by those of skill in the art, measurement and image processing techniques are adaptable to be applicable to both micro-architecture and macro-anatomical structures. Examples of these measurements are shown in Table 2.

As noted above, analysis can also include one or more additional techniques, for example, Hough transform, mean pixel intensity analysis, variance of pixel intensity analysis, soft tissue analysis and the like. See, e.g., co-owned International Application WO 02/30283.

Calibrated density typically refers to the measurement of intensity values of features in images converted to its actual material density or expressed as the density of a reference material whose density is known. The reference material can be metal, polymer, plastics, bone, cartilage, etc., and can be part of the object being imaged or a calibration phantom placed in the imaging field of view during image acquisition.

Extracted structures typically refer to simplified or amplified representations of features derived from images. Bone structure parameters include, for example, micro-structure parameters and macro-structure parameters. Micro-structure parameters could be, for example, the measurements in Table 1. Macro-structure parameters could be; for example, the parameters in Table 2. An example would be binary images of trabecular patterns generated by background subtraction and thresholding. Another example would be binary images of cortical bone generated by applying an edge filter and thresholding. The binary images can be superimposed on gray level images to generate gray level patterns of structure of interest.

Distance transform typically refers to an operation applied on binary images where maps representing distances of each 0 pixel to the nearest 1 pixel are generated. Distances can be calculated by the Euclidian magnitude, city-block distance, La Place distance or chessboard distance.

Distance transform of extracted structures typically refers to distance transform operation applied to the binary images of extracted structures, such as those discussed above with respect to calibrated density.

Skeleton of extracted structures typically refers to a binary image of 1 pixel wide patterns, representing the centerline of extracted structures. It is generated by applying a skeletonization or medial transform operation, by mathematical morphology or other methods, on an image of extracted structures.

Skeleton segments typically are derived from skeleton of extracted structures by performing pixel neighborhood analysis on each skeleton pixel. This analysis classifies each skeleton pixel as a node pixel or a skeleton segment pixel. A node pixel has more than 2 pixels in its 8-neighborhood. A skeleton segment is a chain of skeleton segment pixels continuously 8-connected. Two skeleton segments are separated by at least one node pixel.

Watershed segmentation as it is commonly known to a person of skill in the art, typically is applied to gray level images to characterize gray level continuity of a structure of interest. The statistics of dimensions of segments generated by the process are, for example, those listed in Table 1 above. As will be appreciated by those of skill in the art, however, other processes can be used without departing from the scope of the invention. As described in the Examples, watershed transformation may be applied as follows. The image (or its negative, depending on whether peaks or valleys are to be located) is considered as a topographic relief, in which higher intensities correspond to higher topographic heights. This relief can be divided (segmented) into catchment basins, one for each local minimum of the image, where a catchment basin is defined as the area in which a raindrop would flow to the corresponding minimum. The lines that separate catchment basins from each other are the watersheds.

At step 109, the extracted image data obtained at step 107 can be converted to a 2D pattern, a 3D pattern or a 4D pattern, for example including velocity or time, to facilitate data analyses. Following conversion to 2D, 3D or 4D pattern the images are evaluated for patterns at step 111. Additionally images can be converted from 2D to 3D, or from 3D to 4D, if desired according to step 110. Persons of skill in the art will appreciate that similar conversions can occur between 2D and 4D in this process or any process illustrated in this invention.

As will be appreciated by those of skill in the art, the conversion step is optional and the process can proceed directly from extracting image data from the ROI at step 107 to evaluating the data pattern at step 111. Evaluating the data for patterns, includes, for example, performing the measurements described in Table 1 or Table 2, above.

Additionally, the steps of locating the region of interest, obtaining image data, and evaluating patterns can be performed once or a plurality of times, respectively at any stage of the process. For example, following an evaluation of patterns at step 111, additional image data can be obtained according to step 114, or another region of interest can be located according to step 112. These steps can be repeated as often as desired, in any combination desirable to achieve the data analysis desired.

An alternative process includes the step of enhancing image data prior to converting an image or image data to a 2D, 3D, or 4D pattern. The process of enhancing image data, can be repeated if desired. In still further embodiments, the step of enhancing image data may occur after converting an image or image data to a 2D, 3D, or 4D pattern. Again, the process of enhancing image data, can be repeated if desired.

Furthermore, in certain embodiments, after locating a part of the body for study and imaging, the image is then converted to a 2D pattern, 3D pattern or 4D pattern. The region of interest is optionally located within the image after optional conversion to a 2D, 3D and/or 4D image and data is then extracted. Patterns are then evaluated in the extracted image data.

Some or all the processes can be repeated one or more times as desired. For example, locating a part of the body for study, locating a region of interest, obtaining image data, and evaluating patterns, can be repeated one or more times if desired, respectively. For example, following an evaluation of patterns, additional image data can be obtained, or another region of interest can be located and/or another portion of the body can be located for study. These steps can be repeated as often as desired, in any combination desirable to achieve the data analysis desired.

Image data may also be enhanced. The step of enhancing image data may occur prior to conversion, prior to locating a region of interest, prior to obtaining image data, or prior to evaluating patterns.

The method also comprises obtaining an image of a bone or a joint, optionally converting the image to a two-dimensional or three-dimensional or four-dimensional pattern, and evaluating the amount or the degree of normal, diseased or abnormal tissue or the degree of degeneration in a region or a volume of interest using one or more of the parameters specified in Table 1 and/or Table 2. By performing this method at an initial time $T_1$, information can be derived that is useful for diagnosing one or more conditions or for staging, or determining, the severity of a condition. This information can also be useful for determining the prognosis of a patient, for example with osteoporosis or arthritis. By performing this method at an initial time $T_1$, and a later time $T_2$, the change, for example in a region or volume of interest, can be determined which then facilitates the evaluation of appropriate steps to take for treatment. Moreover, if the subject is already receiving therapy or if therapy is initiated after time $T_1$, it is possible to monitor the efficacy of treatment. By performing the method at subsequent times, $T_2$-$T_n$, additional data can be acquired that facilitate predicting the progression of the disease as well as the efficacy of any interventional steps that have been taken. As will be appreciated by those of skill in the art, subsequent measurements can be taken at regular time intervals or irregular time intervals, or combinations thereof. For example, it can be desirable to perform the analysis at $T_1$ with an initial follow-up, $T_2$, measurement taken one month later. The pattern of one month follow-up measurements could be performed for a year (12 one-month intervals) with subsequent follow-ups performed at 6 month intervals and then 12 month intervals. Alternatively, as an example, three initial measurements could be at one month, followed by a single six month follow up which is then followed again by one or more one month follow-ups prior to commencing 12 month follow ups. The combinations of regular and irregular intervals are endless, and are not discussed further to avoid obscuring the invention.

Moreover, one or more of the bone structure parameters listed in Tables 1 and 2, and possibly one or more parameters, can be measured. The measurements can be analyzed separately or the data can be combined, for example using statistical methods such as linear regression modeling or correlation. Actual and predicted measurements can be compared and correlated. See, also, Examples described later.

The method for predicting future fracture in a subject can be fully automated such that the measurements of one or more of the bone structure parameters specified in Tables 1 and 2, and possibly one or more other parameters, are done automatically without intervention. As will be appreciated by those of skill in the art, the fully automated analysis is, for example, possible with one or more of the steps involved in predicting future fracture, including, sliding window ROI analysis of such bone parameter(s) to generate bone parameter maps; watershed segmentation of parameter maps to identify possible or likely fracture lines; local structure analysis (e.g., placement of ROI along predicted fracture line and analysis of tracuelar and cortical bone parameters); combining multiple bone parameters; and/or calculations such as multivariate regressions. This process may also include, for example, seed growing, thresholding, atlas and model based segmentation methods, live wire approaches, active and/or deformable contour approaches, contour tracking, texture based segmentation methods, rigid and non-rigid surface or volume registration, for example based on mutual information or other similarity measures. One skilled in the art will readily recognize other techniques and methods for fully automated assessment of the parameters and measurements described herein.

Alternatively, the method of predicting future fractures in a subject can be semi-automated such that the measurements of one or more of the parameters, including at least one bone structure parameter, are performed semi-automatically, i.e., with intervention. The semi-automatic assessment allows for human interaction and, for example, quality control, and utilizing the measurement of such parameter(s) to diagnose, stage, prognosticate or monitor a disease or to monitor a therapy. The semi-automated measurement is, for example, possible with image processing techniques such as segmentation and registration. This can include seed growing, thresholding, atlas and model based segmentation methods, live wire approaches, active and/or deformable contour approaches, contour tracking, texture based segmentation methods, rigid and non-rigid surface or volume registration, for example base on mutual information or other similarity measures. One skilled in the art will readily recognize other techniques and methods for semi-automated assessment of such parameters.

Following the step of deriving quantitative and/or qualitative image data, one or more candidate agents can be administered to the patient. The candidate agent can be any agent the effects of which are to be studied. Agents can include any substance administered or ingested by a subject, for example, molecules, pharmaceuticals, biopharmaceuticals, agropharmaceuticals, or combinations thereof, including cocktails, that are thought to affect the quantitative and/or qualitative parameters that can be measured in a region of interest. These agents are not limited to those intended to treat disease that affects the musculoskeletal system but this invention is intended to embrace any and all agents regardless of the intended treatment site. Thus, appropriate agents are any agents whereby an effect can be detected via imaging. The steps of locating a region of interest, obtaining image data, obtaining such quantitative and/or qualitative data from image data, and administering a candidate agent, can be repeated one or more times as desired, respectively. Image data may be enhanced as often as desired.

Furthermore, an image may be taken prior to administering the candidate agent. However, as will be appreciated by those of skill in the art, it is not always possible to have an image prior to administering the candidate agent. In those situations, progress is determined over time by evaluating the change in parameters from extracted image to extracted image.

The derived quantitative and/or qualitative information can be compared to an image taken at T1, or any other time, if such image is available. Again, the steps of deriving information and/or enhancing data can be repeated, as desired.

In addition, following the step of extracting image data from the ROI, the image can be transmitted. Transmission can be to another computer in the network or via the World Wide Web to another network. Following the step of transmitting the image, the image is converted to a pattern of normal and diseased tissue. Normal tissue includes the undamaged tissue located in the body part selected for study. Diseased tissue includes damaged tissue located in the body part selected for study. Diseased tissue can also include, or refer to, a lack of normal tissue in the body part selected for study. For example, damaged or missing bone would be considered diseased tissue. Once the image is converted, it may be analyzed.

The step of transmitting the image is optional. As will be appreciated by those of skill in the art, the image can also be analyzed prior to converting the image to a pattern of normal and diseased.

As previously described, some or all the processes can be repeated one or more times as desired. For example, locating a region of interest, obtaining image data, enhancing image data, transmitting an image, converting the image to a pattern of normal and diseased, analyzing the converted image, can be repeated one or more times if desired, respectively.

Two or more devices may be connected. Either the first or second device can develop a degeneration pattern from an image of a region of interest. Similarly, either device can house a database for generating additional patterns or measurements. The first and second devices can communicate with each other in the process of analyzing an image, developing a degeneration pattern from a region of interest in the image, creating a dataset of patterns or measurements or comparing the degeneration pattern to a database of patterns or measurements. However, all processes can be performed on one or more devices, as desired or necessary.

In this method the electronically generated, or digitized image or portions of the image can be electronically transferred from a transferring device to a receiving device located distant from the transferring device; receiving the transferred image at the distant location; converting the transferred image to a pattern of normal or diseased or abnormal tissue using one or more of the parameters specified in Table 1 or Table 2; and optionally transmitting the pattern to a site for analysis. As will be appreciated by those of skill in the art, the transferring device and receiving device can be located within the same room or the same building. The devices can be on a peer-to-peer network, or an intranet. Alternatively, the devices can be separated by large distances and the information can be transferred by any suitable means of data transfer, including http and ftp protocols.

Alternatively, the method can comprise electronically transferring an electronically-generated image or portions of an image of a bone or a joint from a transferring device to a receiving device located distant from the transferring device; receiving the transferred image at the distant location; converting the transferred image to a degeneration pattern or a pattern of normal or diseased or abnormal tissue using one or more of the parameters specified in Table 1 or Table 2; and optionally transmitting the degeneration pattern or the pattern of normal or diseased or abnormal, tissue to a site for analysis.

Thus, the invention described herein includes methods and systems for prognosis of fracture risk. (See, also, Examples).

In order to make more accurate prognoses, it may be desirable in certain instances to compare data obtained from a subject to a reference database. For example, when predicting fracture risk, it may be useful to compile data of actual (known) fracture load in a variety of samples and store the results based on clinical risk factors such as age, sex and weight (or other characteristics) of the subject from which the sample is obtained. The images of these samples are analyzed to obtain parameters shown in Tables 1 and 2, and possibly one or more other parameters. A fracture risk model correlated with fracture load may be developed using univariate, bivariate and/or multivariate statistical analysis of these parameters and is stored in this database. A fracture risk model may include information that is used to estimate fracture risk from parameters shown in Tables 1 and 2, and possibly one or more other parameters. An example of a fracture risk model is the coefficients of a multivariate linear model derived from multivariate linear regression of these parameters (Tables 1, 2, age, sex, weight, etc.) with fracture load. A person skilled in the art will appreciate that fracture risk models can be derived using other methods such as artificial neural networks and be represented by other forms such as the coefficients of artificial neural networks. Patient fracture risk can then be determined from measurements obtain from bone images by referencing to this database.

In conventional methods of determining actual fracture load, cross-sectional images may be taken throughout testing to determine at what load force a fracture might occur.

Figure 5:
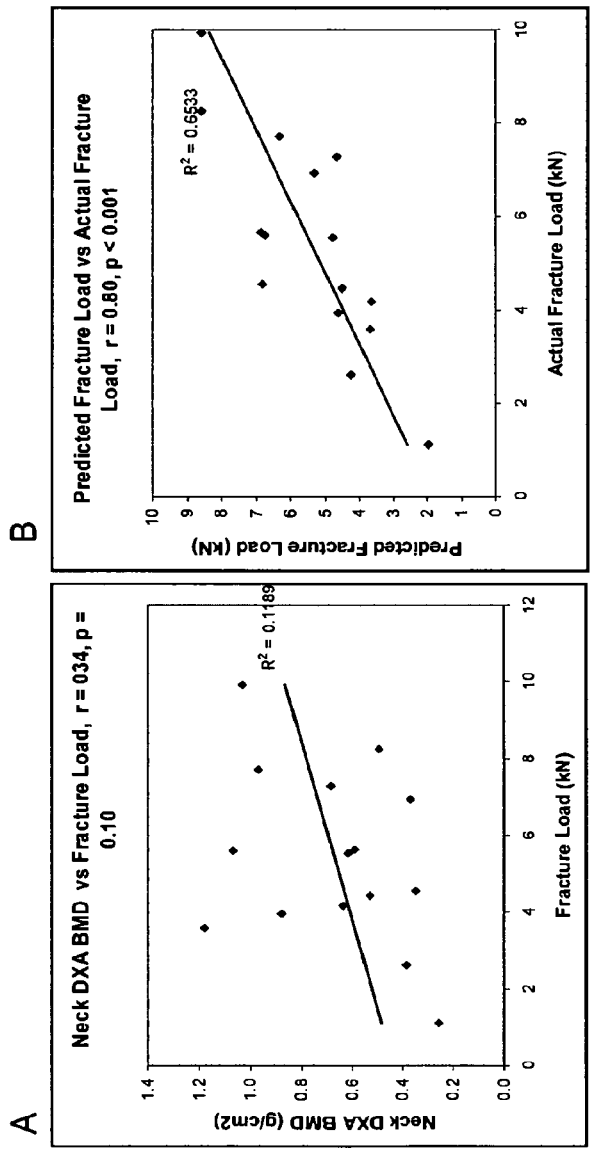
FIGS. 5A and 5B are graphs depicting correlation of femoral neck DXA bone mineral density (BMD) and fracture load (FIG. 5A) and correlation of predicted fracture load and actual fracture load (FIG. 5B) according to a conventional method.

The analysis techniques described herein can then be applied to a subject and the risk of fracture (or other disease) could be predicted using one or more of the parameters described herein. The prognostication methods described herein are more accurate than conventional methods for predicting fracture risk. FIG. 5A is a graph depicting conventional linear, regression analysis of DXA bone mineral density correlated to fracture load. Correlations of individual parameters to fracture load are comparable to DXA. However, when multiple structural parameters are combined, the prediction of load at which fracture will occur is more accurate. Thus, the analyses of images as described herein can be used to accurately predict musculoskeletal disease such as fracture risk.

Another aspect of the present invention is a kit for aiding in predicting fracture risk in a subject, which kit comprises a software program, which when installed and executed on a computer creates a bone parameter map (e.g., using one or more of the parameters specified in Tables 1 and 2, and possibly one or more other parameters) presented in a standard graphics format and produces a computer readout. The kit can further include software for (1) identifying likely fracture lines (e.g., by watershed segmentation); (2) placing one or more ROI along predicted fracture line(s); (3) analyzing one or more bone parameters along predicted fracture lines; and/or (4) combining multiple bone parameters and calculating fracture load.

The kit can further include one or more databases of measurements for use in calibrating or diagnosing the subject. One or more databases can be provided to enable the user to compare the results achieved for a specific subject against, for example, a wide variety of subjects, or a small subset of subjects having characteristics similar to the subject being studied.

A system is provided that includes (a) a device for electronically transferring an image, a parameter map, an analyzed parameter map, etc., to a receiving device located distant from the transferring device; (b) a device for receiving the image or map at the remote location; (c) a database accessible at the remote location for generating additional patterns or measurements for the bone or the joint of a subject wherein the database includes a collection of subject patterns or data, for example of human bones or joints, which patterns or data are organized and can be accessed by reference to characteristics such as type of joint, gender, age, height, weight, bone size, type of movement, and distance of movement; and (d) optionally a device for transmitting the correlated pattern back to the source of the degeneration pattern or pattern of normal, diseased or abnormal tissue.

Thus, the methods and systems described herein may make use of collections of data sets of measurement values, for example measurements of bone structure, probably with other measurements from images (e.g., x-ray images). Records can be formulated in spreadsheet-like format, for example including data attributes such as date of image (x-ray), patient age, sex, weight, current medications, geographic location, etc. The database formulations can further comprise the calculation of derived or calculated data points from one or more acquired data points, typically using the parameters listed in Tables 1 and 2 or combinations thereof. A variety of derived data points can be useful in providing information about individuals or groups during subsequent database manipulation, and are therefore typically included during database formulation. Derived data points include, but are not limited to the following: (1) maximum value of a selected bone structure parameter, determined for a selected region of bone or joint or in multiple samples from the same or different subjects; (2) minimum value of a selected bone structure parameter, determined for a selected region of bone or joint or in multiple samples from the same or different subjects; (3) mean value of a selected bone structure parameter, determined for a selected region of bone or joint or in multiple samples from the same or different subjects; (4) the number of measurements that are abnormally high or low, determined by comparing a given measurement data point with a selected value; and the like. Other derived data points include, but are not limited to the following: (1) maximum value of bone mineral density, determined for a selected region of bone or in multiple samples from the same or different subjects; (2) minimum value of bone mineral density, determined for a selected region of bone or in multiple samples from the same or different subjects; (3) mean value of bone mineral density, determined for a selected region of bone or in multiple samples from the same or different subjects; (4) the number of bone mineral density measurements that are abnormally high or low, determined by comparing a given measurement data point with a selected value; and the like. Other derived data points will be apparent to persons of ordinary skill in the art in light of the teachings of the present specification. The amount of available data and data derived from (or arrived at through analysis of) the original data provides an unprecedented amount of information that is very relevant to management of musculoskeletal-related diseases such as osteoporosis or arthritis. For example, by examining subjects over time, the efficacy of medications can be assessed.

Measurements and derived data points are collected and calculated, respectively, and can be associated with one or more data attributes to form a database.

Data attributes can be automatically input with the electronic image and can include, for example, chronological information (e.g., DATE and TIME). Other such attributes can include, but are not limited to, the type of imager used, scanning information, digitizing information and the like. Alternatively, data attributes can be input by the subject and/or operator, for example subject identifiers, i.e., characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., disease states or conditions, etc.); and (5) disease-associated characteristics such as the type of bone disorder, if any; the type of medication used by the subject. In the practice of the present invention, each data point would typically be identified with the particular subject, as well as the demographic, etc. characteristic of that subject.

Other data attributes will be apparent to persons of ordinary skill in the art in light of the teachings of the present specification. (See, also, WO 02/30283).

Thus, data about bond structure information, possibly with bone mineral density information and/or articular information, is obtained from normal control subjects using the methods described herein. These databases are typically referred to as "reference databases" and can be used to aid analysis of any given subject's image, for example, by comparing the information obtained from the subject to the reference database. Generally, the information obtained from the normal control subjects will be averaged or otherwise statistically manipulated to provide a range of "normal" measurements. Suitable statistical manipulations and/or evaluations will be apparent to those of skill in the art in view of the teachings herein. The comparison of the subject's information to the reference database can be used to determine if the subject's bone information falls outside the normal range found in the reference database or is statistically significantly different from a normal control.

Data obtained from images, as described above, can be manipulated, for example, using a variety of statistical analyses to produce useful information. Databases can be created or generated from the data collected for an individual, or for a group of individuals, over a defined period of time (e.g., days, months or years), from derived data, and from data attributes.

For example, data can be aggregated, sorted, selected, sifted, clustered and segregated by means of the attributes associated with the data points. A number of data mining software exist which can be used to perform the desired manipulations.

Relationships in various data can be directly queried and/or the data analyzed by statistical methods to evaluate the information obtained from manipulating the database.

For example, a distribution curve can be established for a selected data set, and the mean, median and mode calculated therefor. Further, data spread characteristics, e.g., variability, quartiles, and standard deviations can be calculated.

The nature of the relationship between any variables of interest can be examined by calculating correlation coefficients. Useful methods for doing so include, but are not limited to: Pearson Product Moment Correlation and Spearman Rank Correlation. Analysis of variance permits testing of differences among sample groups to determine whether a selected variable has a discernible effect on the parameter being measured.

Non-parametric tests can be used as a means of testing whether variations between empirical data and experimental expectancies are attributable to chance or to the variable or variables being examined. These include the Chi Square test, the Chi Square Goodness of Fit, the 2×2 Contingency Table, the Sign Test and the Phi Correlation Coefficient. Other tests include z-scores, T-scores or lifetime risk for arthritis, cartilage loss or osteoporotic fracture.

There are numerous tools and analyses available in standard data mining software that can be applied to the analyses of the databases that can be created according to this invention. Such tools and analysis include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory driven, relationships.

Statistical significance can be readily determined by those of skill in the art. The use of reference databases in the analysis of images facilitates that diagnosis, treatment and monitoring of bone conditions such as osteoporosis.

For a general discussion of statistical methods applied to data analysis, see Applied Statistics for Science and Industry, by A. Romano, 1977, Allyn and Bacon, publisher.

The data is preferably stored and manipulated using one or more computer programs or computer systems. These systems will typically have data storage capability (e.g., disk drives, tape storage, optical disks, etc.). Further, the computer systems can be networked or can be stand-alone systems. If networked, the computer system would be able to transfer data to any device connected to the networked computer system for example a medical doctor or medical care facility using standard e-mail software, a central database using database query and update software (e.g., a data warehouse of data points, derived data, and data attributes obtained from a large number of subjects). Alternatively, a user could access from a doctor's office or medical facility, using any computer system with Internet access, to review historical data that can be useful for determining treatment.

If the networked computer system includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as can be necessary if the database server is distributed over two or more different computers.

As a person of skill in the art will appreciate, one or more of the parameters specified in Table 1 and Table 2 can be used at an initial time point $T_1$ to assess the severity of a bone disease such as osteoporosis. The patient can then serve as their own control at a later time point $T_2$, when a subsequent measurement using one or more of the same parameters used at $T_1$ is repeated.

A variety of data comparisons can be made that will facilitate drug discovery, efficacy, dosing, and comparisons. For example, one or more of the parameters specified in Table 1 and Table 2 may be used to identify lead compounds during drug discovery. For example, different compounds can be tested in animal studies and the lead compounds with regard to the highest therapeutic efficacy and lowest toxicity, e.g. to the bone or the cartilage, can be identified. Similar studies can be performed in human subjects, e.g., FDA phase I, II or III trials. Alternatively, or in addition, one or more of the parameters specified in Table 1 and Table 2 can be used to establish optimal dosing of a new compound. It will be appreciated also that one or more of the parameters specified in Table 1 and Table 2 can be used to compare a new drug against one or more established drugs or a placebo. The patient can then serve as their own control at a later time point $T_2$.

EXAMPLES

Example 1

Correlation of Micro-Structural and Macro-Structural Parameters to Fracture Load Using 15 fresh cadaveric femurs, the following analyses were performed to determine the correlation of various micro-structural and macro-structural parameters to fracture load, as determined by biomechanical testing. Parameters measured included one or more of the following

| Parameter Name | Description |
|---|---|
| | Measurements on gray values of extracted structures |
| Std. dev. of normalized ROI | Normalized ROI is subtracted from the background using a difference of gaussian filter. The standard deviation reflects the "roughness" of the trabecular structures. |
| | Measurements on binarization of extracted structures |
| Trab. Perimeter | Total length of outline (perimeter) of extracted trabecular structures in a ROI. |
| Trab. Perimeter/Trab. Area | Trabecular perimeter normalized by area of extracted trabecular structures. |
| Trab. Perimeter/Total Area | Trabecular perimeter normalized by ROI area. |
| Trabecular Bone Pattern Factor | Change of perimeter per change of area. Measures concavity and convexity of structures. |
| Trabecular Star Volume | Estimated volume of trabecular structures by measuring distance of random points to boundaries of extracted structures. |
| Marrow Space Length | Mean length of skeletonized marrow space (background) region. |
| Mode Trab. Separation | The mode of distance transform values of the marrow space (background) region. |
| Std. Dev of Trabecular Separation | The standard deviation of distance transform values of the marrow space (background) region. |
| Trabecular Separation | The mean of distance transform values of the marrow space region. |
| Trabecular Thickness | The mean of distance transform values along the skeleton (centerline) of extracted structures. |
| Max. Trab. | The maximum distance transform value of extracted structures in an ROI. |

| Parameter Name | Description |
|---|---|
| Thickness | |
| Measurements on skeleton of extracted structures | |
| Trabecular Segment Thickness | The mean of distance transform values along the segmented (by nodes) skeleton of extracted structures. |
| Free-end Segment Thickness | The mean of distance transform values along the free-end segments of the skeletonized structures. |
| Node-Node Segment Thickness | The mean of distance transform values along the node-node (inner) segments of the skeletonized structures. |
| Number of Nodes | Number of nodes (branching points) of skeletonized structures normalized by ROI area. |
| Segment Number | Number of skeleton segments normalized by ROI area. |
| Free-end Segment Number | Number of free-end skeleton segments normalized by ROI area. |
| Segment Tortuosity | Ratio of length of segments to distance between segment ends. |
| Segment Solidity | Ratio of length of segment to area of convex hull of the segment. |
| Watershed segmentation is applied to normalized gray level images. Statistics of watershed segments are: | |
| Watershed Segment Area | Average area of watershed segments. Measures the trabecular separation by area between structures. |
| Watershed Segment Number | Number of watershed segments normalized by ROI area. |
| Std. dev. of Watershed Area | Standard deviation of areas of watershed segments. Measures the homogeneity of trabecular separation |
| Macro-anatomical and geometric parameters | |
| Median Cortical Thickness | Median of distance transform values measured along the centerline of extracted cortical bone structure. |
| Maximum Cortical Thickness | Maximum of distance transform values measured along the centerline of extracted cortical bone structure. |
| Hip Axis Length | Length of the femoral neck axis, extending from the bone edge at the base of trochanter to the bone edge at the inner pelvic brim (femoral head for cadaveric femur). |
| Neck-shaft angle | Angle between femoral neck axis and shaft axis. |
| Head diameter | Largest cross section of femoral head. |
| Mean Neck Width | Mean of distance transform on femoral neck axis between center of femoral head to intertrochanteric line. |
| Minimum Neck Width | Minimum distance transform value on femoral neck axis. |

Standardization of Hip Radiographs:

Density and magnification calibration on the x-ray radiographs was achieved using a calibration phantom. The reference orientation of the hip x-rays was the average orientation of the femoral shaft.

Automatic Placement of Regions of Interest.

Seven regions of interest were consistently and accurately placed based on the geometry and position of the proximal femur (FIG. 2). This was achieved by detecting femoral boundaries, estimating shaft and neck axes, and constructing the ROIs based on axes and boundary intercept points. This approach ensured that the size and shape of ROIs placed conformed to the scale and shape of the femur, and thus were consistent relative to anatomic features on the femur.

Automatic Segmentation of the Proximal Femur:

A global gray level thresholding using bi-modal histogram segmentation algorithm(s) was performed on the hip images and a binary image of the proximal femur was generated. Edge-detection analysis was also performed on the hip x-rays, including edge detection of the outline of the proximal femur that involved breaking edges detected into segments and characterizing the orientation of each segment. Each edge segment was then referenced to a map of expected proximal femur edge orientation and to a map of the probability of edge location. Edge segments that did not conform to the expected orientation or which were in low probability regions were removed. Morphology operations were applied to the edge image(s) to connect any discontinuities. The edge image formed an enclosed boundary of the proximal femur. The region within the boundary was then combined with the binary image from global thresholding to form the final mask of the proximal femur.

Automatic Segmentation and Measurement of the Femoral Cortex:

Within a region of interest (ROI), edge detection was applied. Morphology operations were applied to connect edge discontinuities. Segments were formed within enclosed edges. The area and the major axis length of each segment were then measured. The regions were also superimposed on the original gray level, image and average gray level within each region was measured. The cortex was identified as those segments connected to the boundary of the proximal femur mask with the greatest area, longest major axis length and a mean gray level about the average gray level of all enclosed segments within the proximal femur mask.

The segment identified as cortex was then skeletonized. The orientation of the cortex skeleton was verified to conform to the orientation map of the proximal femur edge. Euclidean distance transform was applied to the binary image of the segment. The values of distance transform value along the skeleton were sampled and their average, standard deviation, minimum, maximum and mod determined.

Figure 11:
FIG. 11 depicts definition of a region of interest (ROI) along the predicted fracture path using a region growing technique. This region of interest is used for a structural analysis of the trabecular bone. Contact points between the trabecular ROI and the cortical bone determine the area for cortical bone measurements.

Watershed Segmentation for Characterizing Trabecular Structure:

Marrow spacing was characterized by determining watershed segmentation of gray level trabecular structures on the hip images, essentially as described in Russ "The Image Processing Handbook," 3$^{rd}$. ed. pp. 494-501. This analysis takes the gray level contrast between the marrow spacing and adjacent trabecular structures into account. The segments of marrow spacing generated using watershed segmentation were measured for the area, eccentricity, orientation, and the average gray level on the x-ray image within the segment. Mean, standard deviation, minimum, maximum and mode were determined for each segment. In addition, various micro-structural and/or macro-anatomical parameters were assessed for several ROIs to predict the fracture path, as shown in FIG. 11.

Measurement of Femoral Neck BMD:

MA analysis of bone mineral density was performed in the femoral neck region of the femurs.

Biomechanical Testing of Intact Femur:

Each cadaveric femur sample (n=15) was tested for fracture load as follows. First, the femur was placed at a 15° angle of tilt and an 8° external rotation in an Instron 1331 Instrument (Instron, Inc.) and a load vector at the femoral head simulating single-leg stance was generated, essentially as described in Cheal et al. (1992) *J. Orthop. Res.* 10(3):405-422. Second, varus/valgus and torsional resistive movements simulating passive knee ligament restraints were applied. Next, forces and movement at failure were measured using a six-degree of freedom load cell. Subsequently, a single ramp, axial compressive load was applied to the femoral head of each sample at 100 mm/s until fracture. Fracture load and resultant equilibrium forces and moments at the distal end of the femur were measured continuously.

There was a weak positive correlation of femoral neck BMD (r=0.34, p=0.10) (FIG. 4A) and total BMD with failure load (r=0.28, p=0.15). Radiographs were analyzed in several regions of interest (ROI) at the femoral head, neck and proximal shaft to yield indices of trabecular micro-structure and macro-anatomic indices such as cortical thickness. The micro-structural parameter of Trabecular Segment Thickness from ROI 4 had the strongest failure load correlation coefficient, with r=−0.75. Macro-anatomic indices such as Maximum Cortical Thickness of ROI 6 and Median Cortical Thickness of ROI 5 correlate with failure load with r=0.65 (p=0.005) and r=0.53 (p=0.02), respectively.

Based on these results, Trabecular Segment Thickness and Trabecular Separation from ROI 4 were combined to predict a failure load. Based on results from these 15 femora, correlation between predicted and actual failure loads was r=0.8 (p<0.001) (FIG. 5B). The mean fracture load was 5.4 kiloNewton with a standard deviation of 2.3 kiloNewton. These statistics and the coefficients of multivariate linear regression were stored as data of the fracture load reference database.

Influence of Positioning:

The effects of the femur position were also examined in order to determine a set of measurements that are the most robust against the positioning variations that can occur during imaging.

Radiographs were taken at −15° (external rotation), and at every 5° increment up to +20° of internal rotation (70 kVp, photo-timer, centered on the femoral neck). Variability of a parameter was expressed as the coefficient of variation (COY) of the measurements at each angle. Of all the regions, ROI 4 showed the lowest average (root mean square) COV of the parameters.

As shown in Table 3 below, variability was generally lower for the 5° to 15° range. This was also observed for the other regions of interest. Thus, internal rotation of 5° to 15° provides an acceptable margin of variation for a number of parameters. The regular AP hip x-ray imaging protocol used by technicians is therefore sufficient to control positioning variability.

TABLE 3

| Parameter | Range of Rotation angles (degrees) | | | | |
|---|---|---|---|---|---|
|  | 0...10 | 5...15 | 5...20 | 10...20 | −15...20 |
| Trab. Perimeter/ Total Area | 1.6 | 0.5 | 1.7 | 1.9 | 2.7 |
| Free-end Thickness | 2.6 | 0.5 | 2.7 | 3.3 | 3.7 |
| Segment Tortuosity | 0.8 | 1.0 | 0.9 | 0.7 | 0.8 |
| Trabecular Segment Thickness | 2.5 | 1.0 | 3.6 | 4.1 | 3.0 |
| Trabecular Area Ratio | 2.5 | 1.2 | 6.9 | 7.7 | 5.3 |
| Trabecular Bone Pattern Factor | 1.3 | 1.3 | 4.1 | 4.4 | 3.8 |
| Trabecular Separation | 1.9 | 2.0 | 1.6 | 0.6 | 1.8 |
| Segment Solidity | 4.1 | 2.6 | 4.7 | 5.4 | 3.9 |

Influence of Radiographic Exposure Settings:

The influence of hip x-ray exposure variations on image quality and the subsequent analysis of structural parameters were also tested.

The right hip of a frozen cadaver pelvis was imaged with 60 kVp, 70 kVp, and 80 kVp at 150 mA with automatic exposure using the photo-timer, followed by an exposure one step below and another at one step above the auto exposure, in terms of mAs. An additional image was taken at 75 kVp with the photo timer.

Most parameters exhibited the least variation (across mAs) at 60 kVp, with variability growing with increased kVp. Trabecular separation measurements in ROI 7 had COV's of 2.1%, 4.2% and 5.1% at 60 kVp, 70 kVp and 80 kVp, respectively. These may represent the variability to be expected when using manual time settings in the absence of the automatic phototimer function.

When measurements from only the images captured using the automatic phototimer were considered across kVp (60, 70, 75, 80), the most reproducible measurement was trabecular perimeter, with an average COV of 1.9%.

Our results indicate that the use of a phototimer can markedly reduce the variability of exposures due to subjective kVp setting choices. Radiographs produced with proper and consistent use of the phototimer had acceptable variations of micro-structural and macro-anatomical measurements.

Example 2

Correlation of 2D and 3D Measurements

To demonstrate that these methods that use 2D x-ray technology to quantitatively assess trabecular architecture are as effective as 3D µCT, which serves as a gold standard for such measurements, the following experiments were performed. Bone cores (n=48) were harvested from cadaveric proximal femora. Specimen radiographs were obtained and 2D structural parameters were measured on the radiographs. Cores were then subjected to 3D µCT and biomechanical testing. The µCT images were analyzed to obtained 3D micro-structural measurements. Digitized 2D x-ray images of these cores were also analyzed as described herein to obtain comparative micro-structural measurements.

Figure 3:
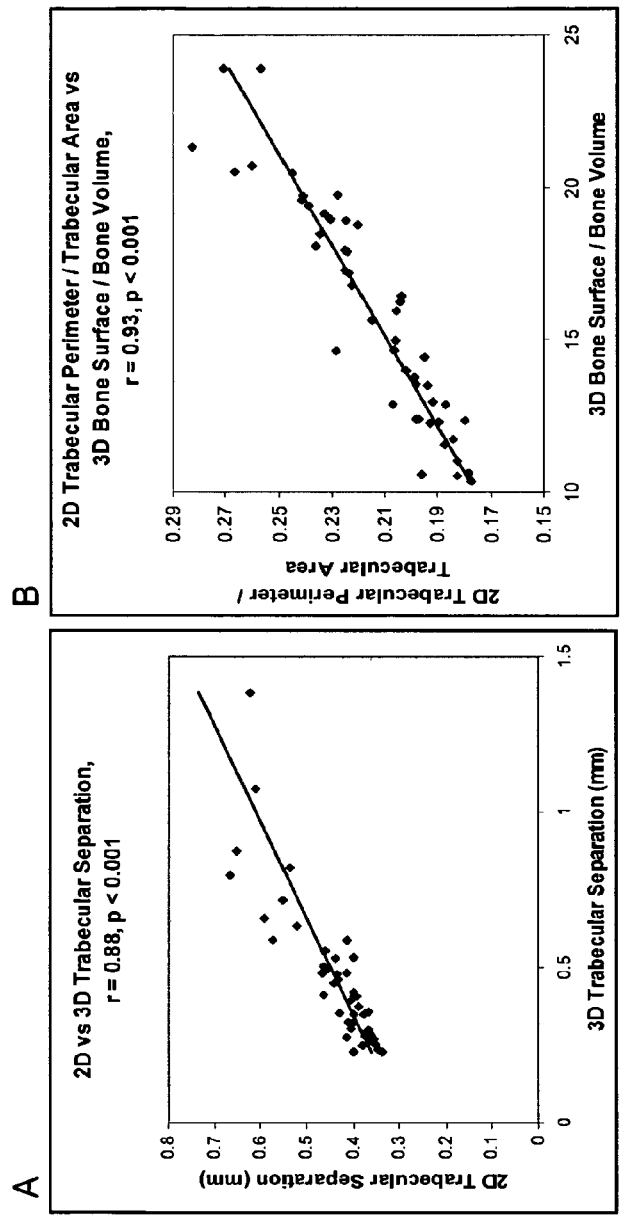
FIGS. 3A and 3B are graphs depicting correlation of 2D and 3D measurements according to one embodiment of the present invention.
Figure 4:
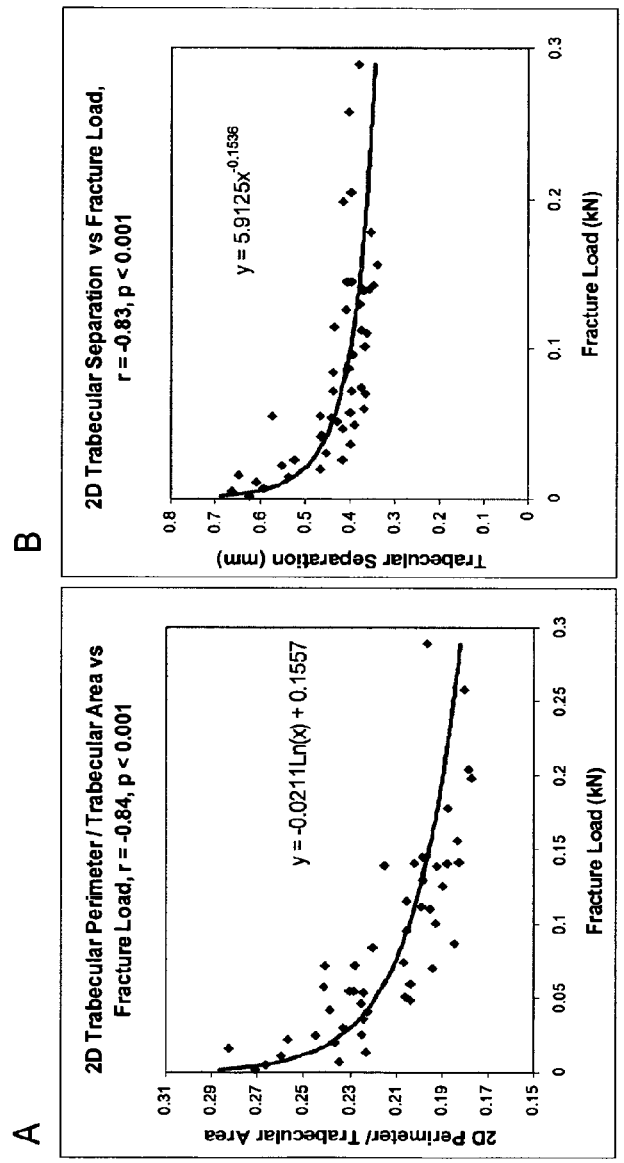
FIGS. 4A and 4B are graphs depicting correlation of 2D measurements with fracture load measurements according to one embodiment of the present invention.

Results showed very good correlation among the numerous 2D parameters and 3D µCT measurements, including for example correlation between 2D Trabecular Perimeter/Trabecular Area (Tb.P/Tb.A) with 3D Bone Surface/Bone Volume (r 0.92, p<0.001), and 2D Trabecular Separation (Tb.Sp) with 3D Trabecular Separation (r=0.88, p<0.001), as shown in FIG. 3. The 2D Tb.P/Tb.A and 2D Tb.Sp also function correlate very well as predictive parameters for the mechanical loads required to fracture the cores, with r=−0.84 (p<0.001) and r=−0.83 (p<0.001), respectively, when logarithmic and exponential transformations were used in the regression, as shown in FIG. 4.

These results demonstrate that 2D micro-structural measurements of trabecular bone from digitized radiographs are highly correlated with 3D measurements obtained from µCT images. Therefore, the mechanical characteristics of trabecular bone micro-structure from digitized radiographic images can be accurately determined from 2D images.

Example 3

Sliding Window Analysis and Watershed

Segmentation

To show feasibility of the approach to better predict an individual's failure load and fracture risk, a sliding window analysis of the proximal femur in 3 cadaveric samples was also performed. Instead of using fixed ROI's as described in FIG. 2, a regular grid was laid over the proximal femur in the x-ray taken before the mechanical failure tests. A rectangular region of interest of a fixed size was placed at each grid node, and bone structure parameters were evaluated within the boundaries of the ROI at each position. This resulted in a value for each bone parameter at each grid node, which was displayed in a color-coded map of the proximal femur for each parameter.

The pre-fracture x-rays were then aligned with the post-fracture images, so that the fracture lines can be shown in the color maps, as shown in FIG. 6. It can be seen in the samples presented in FIG. 6 that certain parameters (e.g., for Area Ratio and Trabecular Perimeter) have a very good agreement between low values ("valleys") in the color maps and the fracture lines, suggesting that a sliding window bone structural analysis can be used to generate a prediction of the exact location where the bone will fracture. The valleys can be found by applying a watershed transformation to the negative values of the parameter maps. For other bone parameters that indicate bone weakness with high values, the watershed transformation can be applied directly to the map.

Example 4

Prediction of Fracture Risk Using Fracture Load Reference Database

A hip x-ray of a cadaver pelvis was exposed using standard clinical procedure and equipment. The radiograph film was developed and digitized. The image was then analyzed to obtain micro-structure, and macro-anatomical parameters. The local maximum spacing, standard deviation of cortical thickness of ROI 3, maximum cortical thickness of ROI 5, and mean node-free end length for ROI 3 were used to predict load required to fracture the cadaver hip using the coefficients of multivariate linear regression stored in the fracture load reference database. The predicted fracture load was 7.5 kiloNewton. This fracture load is 0.98 standard deviation above the average of the fracture load reference database (or z-score=0.98). This result may suggest that the subject had a relatively low risk of sustaining a hip fracture as compared to the population of the reference database.

Example 5

Prediction of Hip Fracture Risk from Radiographic Images

Figure 7A:
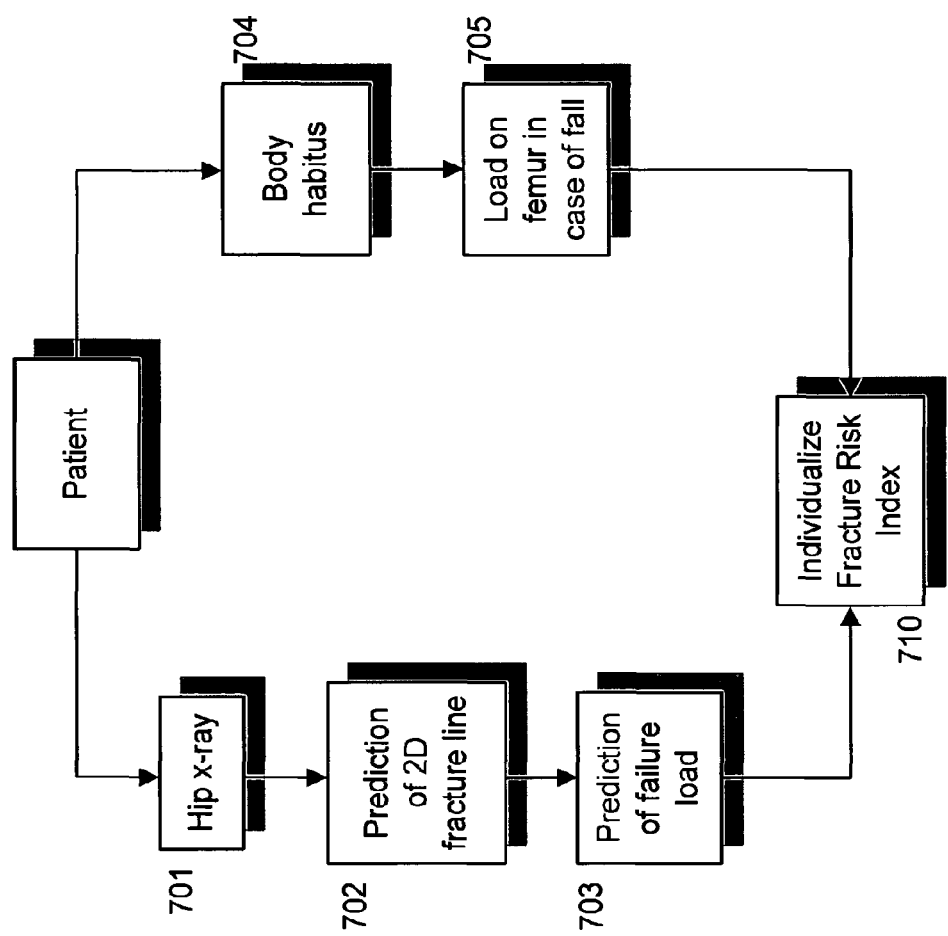
FIGS. 7A and 7B illustrate exemplary steps for predicting fracture risk via individualized fracture risk index (IFRI) according to one embodiment of the present invention.

Individualized hip fracture risk is determined as shown in FIG. 7A. Briefly, an x-ray of the hip is taken at step 701.

At step 702, a 2D fracture line is predicted. The micro- and macro-architecture of the proximal femur in the image is determined by performing automated analyses, as described in Examples 1 and 4. Algorithms for analysis of density, length, thickness, and orientation of trabeculae as well as cortical bone thickness in an ROI in the radiograph are developed using Matlab (The MathWorks, Inc., Natick, Mass.). Similarly, software is developed for automated sliding window analysis (Example 3) of parameters, including at least one bone structure parameter, to produce a distribution map of the proximal femur for each parameter.

In addition, local abnormalities of bone structure are determined from the parameters maps generated as described in Example 3. Regions of high or low values will be evaluated to determine bone strength patterns and used to predict a location of hip fracture.

The parameter maps generated as described in Example 3 are used to identify regions on the bone that have abnormal local structural properties. These regions of high or low values can indicate patterns for stronger or weaker characteristics of bone. The parameter maps generated from the hip x-ray provide a spectrum of trabecular characteristics and can be interpreted as spatial distributions of bone strength. They will be used to predict the location of a hip fracture.

Figure 8:
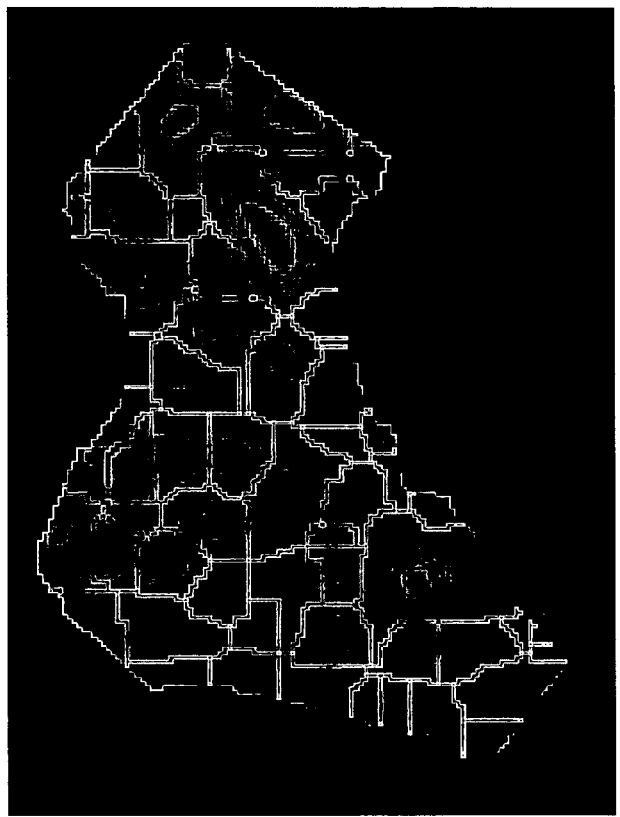
FIG. 8 shows an exemplary bone structure parameter map of a proximal femur. Color scale ranges from blue (low values) to red (high values). Regions are separated along low values ("valleys") using watershed segmentation.

In a first step, depending on the kind of parameter, the low values ("valleys") or high values ("ridges") on the parameter maps are traced using a watershed segmentation operation (see FIG. 8). The resulting boundaries between the regions are regarded as potential fracture lines.

Figure 9:
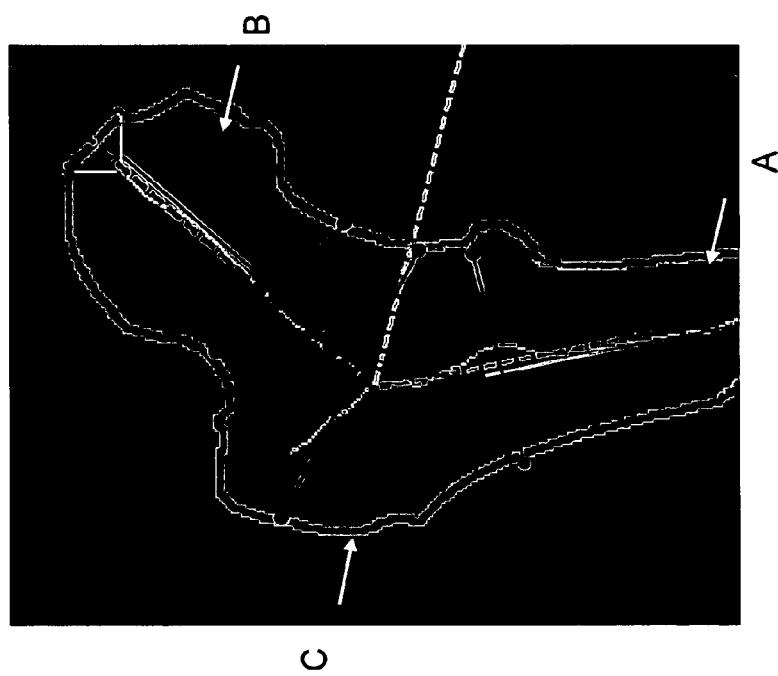
FIG. 9 is an image of a femur and shows an approximation of the femoral axes by two linear segments in the neck (solid blue line) and shaft (solid green line). Also shown is a hyberbolic curve fitted to the intertrochanteric region. White arrows show loading simulating side impact fall. Three examples of cross-sectional lines are also shown.

In a second step, the path along the potential fracture lines that is most likely to coincide with the actual fracture location is determined. A two-dimensional curved beam model as described by Mourtada et al. (1996) *J Orthop Res.* 14(3):483-492 is applied on the thresholded x-ray image of the proximal femur. First, the femoral shaft and neck are approximated by linear axes. The axis in the intertrochanteric region is approximated by a hyperbolic curve that is asymptotic to the linear axes of the femoral neck and shaft, with the focus point at the neck-shaft angle bisector (FIG. 9). Given a loading condition, the internal bending moment, M, is calculated along the neutral axis at 1 mm intervals. For regions where curvature is negligible, the normal stresses along the boundary of the femur are calculated by Equation (1):

$$\sigma_n = \frac{M \cdot x}{CSMI} \quad (1)$$

where CSMI is cross-sectional moment of inertia, and x is the distance from the neutral axis to the point where stress is calculated. Since peak stresses occur on the surfaces, x will be the perpendicular distance of the surface boundary to the neutral axis. Along the curvature, normal stresses can be calculated using Equation (2), $$\sigma_n = \frac{M \cdot x}{CSA \cdot e \cdot (R_{na} - x)} \quad (2)$$

where CSA is the cross-sectional area, e is the distance between the centroid axis and neutral axis, and $R_{na}$ is the radius of curvature of the neutral axis. The loading condition applied to the curved beam model will simulate a fall on the side from standing height with the estimated forces obtained using the methods below. Both CSMI and CSA can be estimated for each cross section by integrating the optical density over the section profile. The relative density and stress values are sufficient for the purpose of locating fracture location. The soft tissue variation was assumed to be insignificant over the proximal femur.

Figure 10:
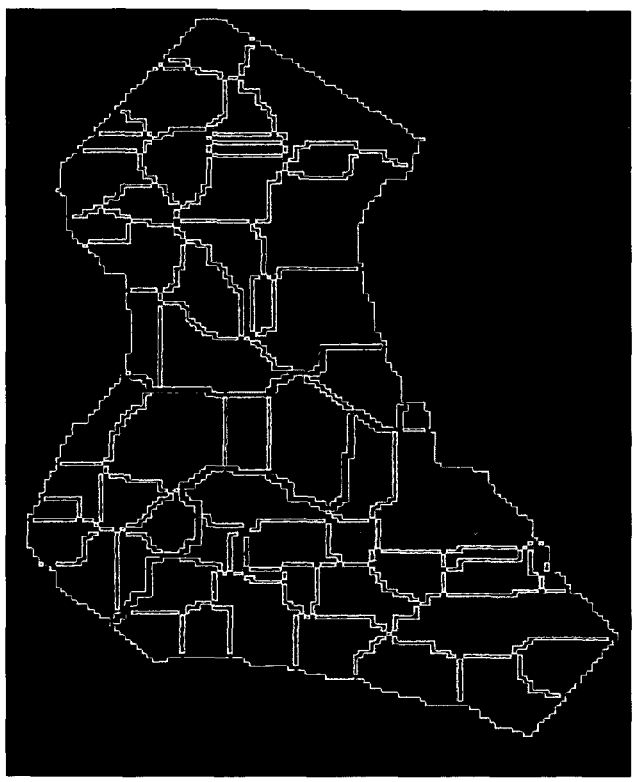
FIG. 10 depicts trochanteric and femoral neck fracture paths (red) that may be constructed by calculating the distance of segments (yellow) to cross-sectional lines (black).

Two common types of fracture, intertrochanteric and femoral neck, will be considered. Two tensile peaks are known to exist on the medial surface for the fall loading condition (see, e.g., Mourtada et al., supra). The peak closer to the bisector of the neck-shaft angle is identified as the starting point of the intertrochanteric fracture, and the other one that is known to be on the posterior surface of the neck, as the starting point for the femoral neck fracture. The cross-sectional lines corresponding to the position of tensile peaks will be considered. The predicted fracture paths will be traced by selecting the watershed boundary segments that are closest to the selected cross-sectional lines (FIG. 10).

To predict the likelihood of intertrochanteric or femoral neck fracture, the values of the parameter map underlying the selected fracture paths will be evaluated and compared. The more likely fracture path will have a lower mean value of a parameter that represents bone strength as optimized by cadaver mechanical loading tests.

At step 703, a local micro- and macro-structural analysis along the predicted fracture line is performed to estimate the load at which the bone will fracture in a particular falling scenario. The case-specific ROI is placed around the predicted fracture line in the trabecular bone using a region growing technique with value constraints. Cortical bone parameters are evaluated in the areas adjacent to the trabecular bone ROI with boundaries determined by perpendicular projection of the outer contact points between trabecular ROI and cortical bone onto the outer contour of the cortical bone (FIG. 11). Multivariate regression will then be used to calculate a failure load $F_{failure}$ from the results of the different bone parameter analyses.

The risk of sustaining an osteoporotic hip fracture does not only depend on the femoral failure load, but also on the impact on the femur in a fall. Factors that influence the severity of the impact are, among others, soft tissue thickness, standing height, and body mass. Impact decreases with increasing soft tissue covering the hip, while it is increased with greater standing height or body mass. The body habitus is calculated at step 704.

Estimation of femoral impact is performed essentially as described in Kroonenberg et al. (1995) *J. Biomech. Eng.* 117(3):309-318. Calculations shown in Equations. (3)-(8) below are based on studies of women. Equations for men can be derived accordingly.

The hip impact velocity is given by Equation (3), $$V = 2.72\sqrt{h} \quad (3),$$

where h is the full body height. The effective mass, i.e., the mass of the part of the body that contributed to the impact force on the hip is calculated as shown in Equation (4):

$$M = \frac{7}{20}m \quad (4)$$

where m is the total body mass.

The peak force on the greater trochanter can then be approximated by Equation (5), at step 705:

$$F_{peak} = V\sqrt{kM} = 1.6\sqrt{hmk} \quad (5)$$

The soft tissue stiffness k correlates negatively with soft tissue thickness (see, Robinovitch et al. (1991) *J. Biomech. Eng* 113:366-374). Fitting the data obtained by Robinovitch et al. for loads with 100 N with a power curve, Equation (6) is obtained:

$$k = 486x^{-0.83} \quad (6)$$

with x being the soft tissue thickness. Soft tissue stiffness dependency on loading force can be approximated by Equation (7):

$$k = 71060 \cdot \left(1 - e^{\frac{-F}{151}}\right) \quad (7)$$

Using Equation. (7) for 100 N, k=34415 N/m for women. Since with Equation (7) soft tissue stiffness plateaus at 71 kN/m for loads expected in a fall, Equation (6) by 71000/34415=2.1 to obtain the relationship between soft tissue thickness and soft tissue stiffness for these higher loads as given by Equation (8):

$$k = 1021x^{-0.83} \quad (8)$$

The soft tissue thickness x will be measured in the hip x-ray laterally between the greater trochanter and the skin.

As discussed above with Example 4, a fracture load reference database can be used for more accurate determination of the fracture load.

At step 710, a measure of fracture risk can then be calculated as the ratio of the peak impact force obtained at step 705 via Equation (5) and the predicted failure load obtained at step 703:

IFRI (Individualized Fracture Risk Index)=
$$F_{peak}/F_{failure} \quad (9)$$

Thus, when the Individualized Fracture Risk Index is low (IFRI<<1), the forces applied to the femur are much lower than required to fracture it, and the bone is at low risk of failure. However, when the IFRI is high (IFRI>>1), failure of the bone is predicted to occur.

Figure 7B:
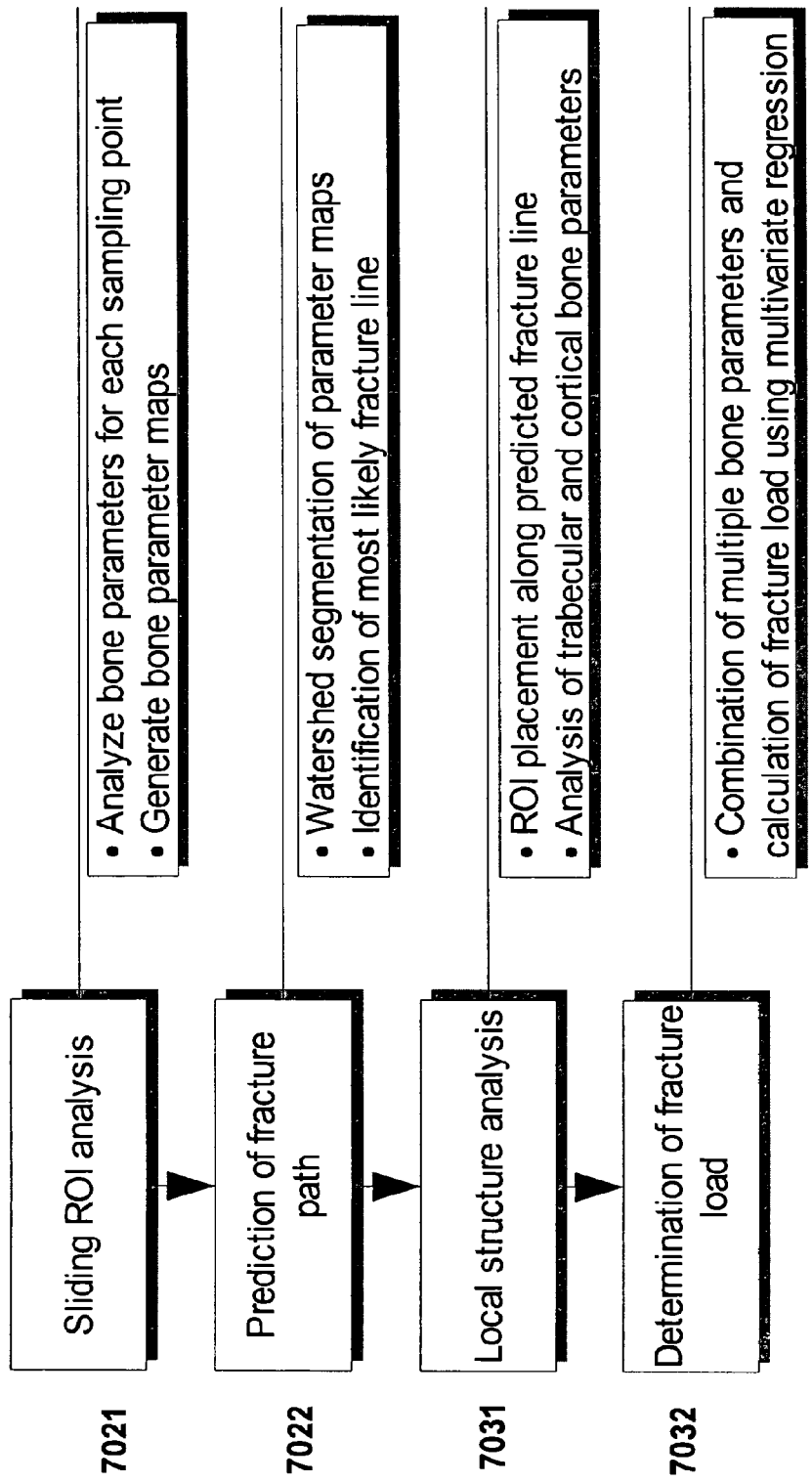

FIG. 7B summarizes the procedure for predicting hip failure load from an x-ray of the proximal femur. As shown, step 702 for predicting fracture lines includes two sub-steps 7021 and 7022. Sub-step 7021 uses sliding ROI analysis to analyze bone parameters, including at least one bone structure parameter, for each sampling point and generate bone parameter maps. Sub-step 7022 uses watershed segmentation of parameter maps to identify most likely fracture lines. Step 703 for predicting the failure load includes sub-steps 7031 and 7032. Sub-step 7031 places ROI along predicted fracture line and analyze trabecular and cortical bone parameters; and sub-step 7032 combines multiple bone parameters and calculates fracture load using multivariate regression.

Figure 12:
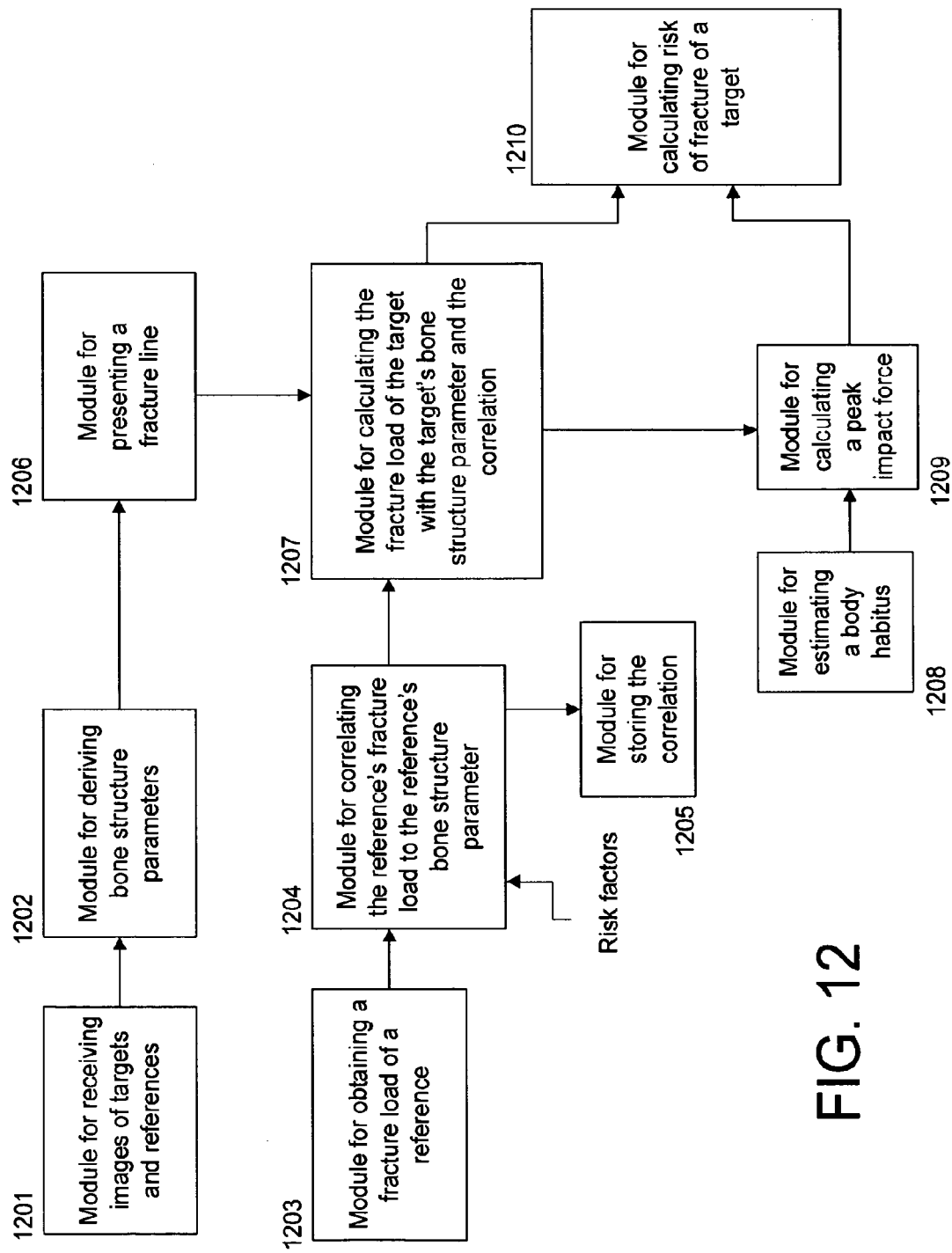
FIG. 12 is a block diagram of a computer program for predicting fracture risk according to one embodiment of the present invention.

FIG. 12 is a block diagram of a computer program used to predict fracture risk according to one embodiment of the present invention. As shown, a module 1201 receives images of skeleton parts of patients and/or references. A module 1202 receives the images from the module 1201 and derives bone structure parameters therefrom. A module 1203 measures a fracture load of a skeleton part of a reference. A module 1204 correlates the reference's fracture load to the reference's bone structure parameter, taking clinical risk factors of the reference into consideration. A module 1205 controls storage of the correlation. A module 1206 generates a parameter map from the derived bone structure parameter of a patient to predict a fracture line. A module 1207 receives the correlation from the module 1204 and the fracture line from the module 1206, and calculates the fracture load of the patient. A module 1208 estimates a body habitus of the patient. A module 1209 receives the body habitus estimation from the module 1208 and the fracture load of the patient from module 1207, and calculates a peak input force. The risk of fracture is predicted at a module 1210 by calculating the ratio between the fracture load of the patient from the module 1207 and the peak impact force from the module 1209.

Although FIG. 12 illustrates modules of a computer program, a skilled artisan would appreciate that hardware and firmware could be used to realize the functions of the modules, and the modules could be distributed at different locations. A suitably programmed computer can constitute hardware counterparts of each of the modules in FIG. 12.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalents.

The invention claimed is:

1. A method for predicting fracture risk using electronic image data of a part of a skeleton of a target in a computer system, the method comprising:
   analyzing at least one bone structure parameter corresponding to at least a portion of the target in one or more regions of interest (ROIs);
   generating a parameter map from a measurement for the at least one bone structure parameter to predict a fracture line;
   analyzing the at least one bone structure parameter along the predicted fracture line to predict a fracture load at which a fracture will occur; and
   predicting a fracture risk by calculating a ratio between the fracture load and a peak impact force on the part of the skeleton of the target using a body habitus of the target;
   comparing the at least one bone structure parameter to a reference parameter to identify a likely location of the fracture; and
   predicting the fracture load of the target with the target's bone structure parameter and a correlation of the reference parameter.

2. The method of claim 1, wherein the peak impact force is estimated.

3. The method of claim 1, wherein the peak impact force is calculated.

4. The method of claim 1, further comprising: generating bone parameter data corresponding to a bone parameter map of at least a portion of the target.

5. The method of claim 4, wherein the data is stored based on clinical risk factors.

6. The method of claim 4, further comprising storing the bone parameter data in a database of bone parameter data.

7. The method of claim 1, wherein the at least one bone structure parameter is at least one parameter from the group consisting of an area ratio, a trabecular perimeter, and combinations thereof.

8. The method of claim 7, wherein the at least one bone structure parameter further comprises a first bone parameter being area ratio and a second bone parameter being trabecular perimeter.

9. The method of claim 4, wherein the parameter map is derived using statistical comparisons of the bone structure parameter to a reference population.

10. The method of claim 1, further comprising identifying local abnormalities of bone structure from the parameter map.

11. The method of claim 1, further comprising: tracing low values or high values on the parameter map; and determining a potential fracture line from the low values or high values.

12. The method of claim 1, further comprising using watershed segmentation of parameter maps to identify the fracture line.

13. The method of claim 1, wherein the at least one bone structure parameter includes at least first and second bone structure parameters, and the method further comprises calculating the fracture load from the first and second bone structure parameters.

14. The method according to claim 1, wherein the body habitus is related to a soft tissue thickness of the target.

15. The method according to claim 1, wherein the body habitus is related to a standing height of the target.

16. The method according to claim 1, wherein the body habitus is related to a body mass of the target.

17. The method of claim 1, wherein the bone structure parameter is a bone micro-structure parameter.

18. The method of claim 1, wherein the bone structure parameter is a bone macro-structure parameter.

19. The method of claim 1, further comprising: transmitting the electronic image data to a second location; converting the electronic image data to a pattern of normal or diseased using the bone structure parameter; and analyzing the converted image.

20. The method of claim 19, further comprising transmitting the pattern to a third location for analyzing.

21. A system for analyzing musculoskeletal-related data of a target using a computer, comprising:
   means for receiving an image of a part of a skeleton of the target;
   means for deriving at least one bone structure parameter from the image;
   means for calculating a possibility of a fracture of the target using the at least one bone structure parameter of the target;

means for analyzing the target's bone structure parameter in one or more regions of interest (ROIs) to predict a possible fracture line and calculate a fracture load of the target;

means for estimating or measuring a body habitus of the target; and means for calculating a peak impact force on the skeleton part when the target falls;

means for obtaining a fracture load of a skeleton part of a reference;

means for correlating a bone structure parameter of the reference to the fracture load of the reference;

means for predicting a fracture risk by calculating a ratio between the fracture load and the peak impact force on the part of the skeleton of the target using a body habitus of the target; and means for receiving the target's bone structure parameter and the correlation of the reference's bone structure parameter, and calculating the fracture load of the target.

22. The system according to claim 21 further comprising means for storing the correlation of the reference's bone structure parameter and the reference's fracture load.

23. The system according to claim 22, wherein the means for storing is configured to receive clinical risk factors of the reference.

* * * * *